(12) United States Patent
Byun et al.

(10) Patent No.: US 8,048,537 B2
(45) Date of Patent: Nov. 1, 2011

(54) CYCLOMETALATED TRANSITION METAL COMPLEX AND ORGANIC LIGHT EMITTING DEVICE USING THE SAME

(75) Inventors: Young-Hun Byun, Yongin-si (KR); Hee-Kyung Kim, Yongin-si (KR); Das Rupasree Ragini, Yongin-si (KR); O-Hyun Kwon, Yongin-si (KR); Yi-Yeol Lyu, Yongin-si (KR); Lyong-Sun Pu, Yongin-si (KR); Shinichiro Tamura, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 984 days.

(21) Appl. No.: 11/634,117

(22) Filed: Dec. 6, 2006

(65) Prior Publication Data

US 2007/0184303 A1 Aug. 9, 2007

(30) Foreign Application Priority Data

Feb. 8, 2006 (KR) .................. 10-2006-0012168

(51) Int. Cl.
*H01L 51/54* (2006.01)
*C09K 11/00* (2006.01)

(52) U.S. Cl. .......... 428/690; 428/917; 252/301.16; 313/504; 313/506; 257/40; 257/102; 257/E51.044; 544/225; 546/10; 548/101; 548/108

(58) Field of Classification Search .............. None
See application file for complete search history.

(56) References Cited

U.S. PATENT DOCUMENTS

| | | | |
|---|---|---|---|
| 4,356,429 A | 10/1982 | Tang | |
| 7,601,438 B2 * | 10/2009 | Ragini et al. | 428/690 |
| 2002/0182441 A1 * | 12/2002 | Lamansky et al. | 428/690 |
| 2003/0059647 A1 * | 3/2003 | Thompson et al. | 428/690 |
| 2003/0080342 A1 * | 5/2003 | Igarashi | 257/79 |
| 2003/0218418 A9 * | 11/2003 | Sato et al. | 313/504 |
| 2004/0053071 A1 * | 3/2004 | Igarashi et al. | 428/690 |
| 2004/0086742 A1 * | 5/2004 | Ma et al. | 428/690 |
| 2005/0170209 A1 * | 8/2005 | Lee et al. | 428/690 |
| 2006/0078760 A1 * | 4/2006 | Ragini et al. | 428/690 |
| 2007/0048546 A1 * | 3/2007 | Ren | 428/690 |

FOREIGN PATENT DOCUMENTS

| | | |
|---|---|---|
| JP | 11-329734 | 11/1999 |
| JP | 2006/104132 | * 4/2006 |

OTHER PUBLICATIONS

You et al. "Inter-ligand energy transfer and related emission change in the cyclometalated heteroleptic iridium complex: facile and efficient color tuning over the whole visible range by the ancillary ligand structure." J. Am. Chem. Soc. 2005, vol. 127, pp. 12438-12439.*

Machine Translation of JP 2006/104132 A (2006).*

F. O. Garces et al., "Synthesis, Structure, Electrochemistry, and Photophysics of Methyl-Substituted Phenylpyridine Ortho-Metalated Iridium(III) Complexes", Inorg. Chem. 1988, 27, 3464-3471.

M. A. Baldo et al., "highly efficient phosphorescent emission from organic electroluminescent devices", Nature, vol. 395, Sep. 10, 1998, pp. 151-154.

Kuwabara et al., "Thermally Stable Multilayered Organic Electroluminescent Devices Using Novel Starburst Molecules, 4,4',4"-Tri(*N*-carbazolyl)triphenylamine (TCTA) and 4,4',4"-Tri(3-methylphenylphenyl-amino)triphenylamine (*m*-MTDATA), as Hole-Transport Materials", Adv. Mater. 1994, 6, No. 9, pp. 677-679.

S. Sprouse et al., "Photophysical Effects of Metal-Carbon σ Bonds in Ortho-Metalated Complexes of Ir(III) and Rh(III)", J. Am. Chem. Soc. 1984, 106, 6647-6653.

* cited by examiner

*Primary Examiner* — Callie Shosho
*Assistant Examiner* — Michael H Wilson
(74) *Attorney, Agent, or Firm* — Robert E. Bushnell, Esq.

(57) ABSTRACT

Provided is a cyclometalated transition metal complex represented by Formula 1:

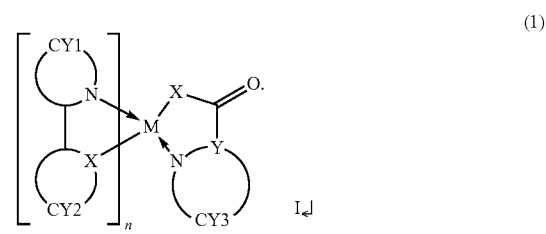

(1)

The cyclometalated transition metal complex contains a new ancillary ligand having a carboxylate acid or the like connected to a hetero ring, so that it can efficiently emit red light from a phosphorous material through intersystem crossing (ISC) to form triplet excitons and then metal to ligand charge transfer (MLCT). An organic light emitting device manufactured using the transition metal complex shows excellent luminous efficiency and external quantum efficiency.

20 Claims, 4 Drawing Sheets

US 8,048,537 B2

CYCLOMETALATED TRANSITION METAL COMPLEX AND ORGANIC LIGHT EMITTING DEVICE USING THE SAME

CROSS-REFERENCE TO RELATED PATENT APPLICATIONS AND CLAIM OF PRIORITY

This application claims the benefit of Korean Patent Application No. 10-2006-0012168, filed on Feb. 8, 2006, in the Korean Intellectual Property Office, the disclosure of which is incorporated herein in its entirety by reference.

BACKGROUND OF THE INVENTION

1. Field of the Invention

The present invention relates to a cyclometalated transition metal complex and an organic light emitting device manufactured using the same, and more particularly, to a cyclometalated transition metal complex that can emit red light by metal-to-ligand charge transfer (MLCT) and an organic light emitting device manufacture that includes an organic layer containing the cyclometalated transition metal complex.

2. Description of the Related Art

Organic light emitting devices (organic EL devices) are self-emission display device in which when a current is provided to a fluorescent or phosphor organic compound layer (hereinafter, referred to as organic layer), electrons and holes are combined together in the organic layer, thereby emitting light. Organic EL devices are lightweight, can be easily manufactured using few components, and have high image quality and wide viewing angles. In addition, they can realize a high degree of color purity and moving pictures, require low power consumption, and operate at low voltages. Due to these advantages, they are suitable for use in portable electronics.

In a general structure of an organic EL device, an anode is formed on a substrate, and a hole transport layer, an emission layer, an electron transport layer, and a cathode are sequentially formed on the anode. The hole transport layer, the emission layer, and the electron transport layer are organic layers formed of organic compounds. An operational principle of an organic EL device having such a structure will now be described in detail. When a voltage is applied between the anode and the cathode, holes injected from the anode move to the emission layer through the hole transport layer, and electrons that are injected from the cathode move to the emission layer through the electron transport layer. In the emission layer, the electrons and holes recombine and thus excitons are generated and light having a wavelength corresponding to a band gap of a material is generated by radiative decay.

According to an emission mechanism, materials that are used to form an emission layer of an organic light emitting device are divided into fluorescent materials that use singlet excitons and phosphor materials that use triplet excitons. These fluorescent and phosphor materials themselves can be used to form an emission layer, or they can be doped on an appropriate host material to form an emission layer. As a result of electron excitation, singlet excitons and triplet excitons are formed in a host. At this time, a statistical generation ratio of singlet excitons to triplet excitons is 1:3.

When an organic light emitting device has an emission layer formed of a fluorescent material, triplet excitons that are generated in a host thereof are not used. On the other hand, when an organic light emitting device has an emission layer formed of a phosphor material, both singlet excitons and triplet excitons can be used such that internal quantum efficiency reaches 100% (Baldo, et al., Nature, Vol. 395, 151-154, 1998). Accordingly, an organic light emitting device that has an emission layer formed of a phosphor material shows much higher luminous efficiency than an organic light emitting device that has an emission layer formed of a fluorescent material.

When a heavy metal, such as Ir, Pt, Rh, or Pd, is introduced to an organic molecule, a triplet state and a singlet state are mixed together through spin-orbital coupling that occurs due to a heavy atom effect, thereby enabling transition that is forbidden and effectively emitting a light using a phosphor material even at room temperature.

Recently, a green light emitting material of which an internal quantum efficiency can reach 100% has been developed using a phosphor material.

Although transition metal complexes containing transition metals, such as Iridium or Platinum, are being developed as a highly efficient emission materials using phosphor materials, their luminous efficiencies are not suitable for highly efficient full-color displays or white light emission applications having low power consumption.

Accordingly, there is a need to develop a red light emitting material having improved properties by overcoming such conventional technical limits on development of red light emitting materials.

SUMMARY OF THE INVENTION

The present invention provides a cyclometalated transition metal complex that efficiently emits red light by triplet metal to ligand charge transfer (MLCT).

The present invention also provides an organic light emitting device that efficiently emits red light.

According to an aspect of the present invention, there is provided a cyclometalated transition metal complex represented by Formula 1:

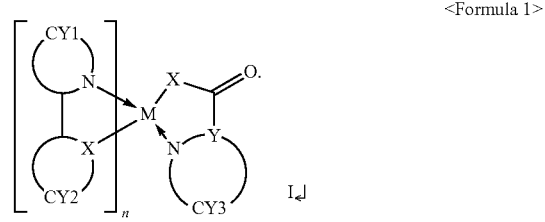

where M is a transition metal;

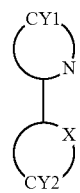

is a first mono anionic bidentate chelating ligand;

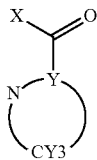

is a second mono anionic bidentate chelating ligand;

X and Y are each independently C, S, O, or N;

CY1, CY2, and CY3 are each independently aromatic or aliphatic rings; and n is 1 or 2.

In the cyclometalated transition metal complex, the first mono anionic bidentate chelating ligand may be selected from ligands represented by formulae below:

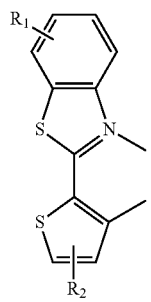
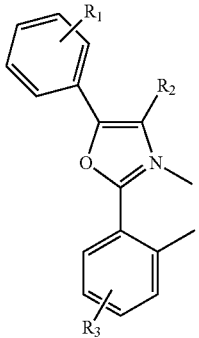
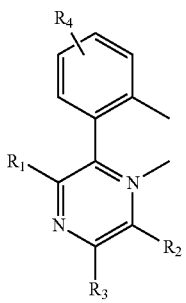
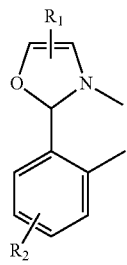
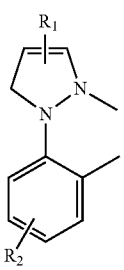
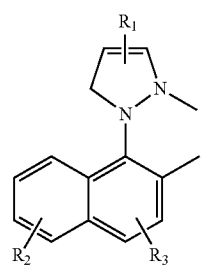

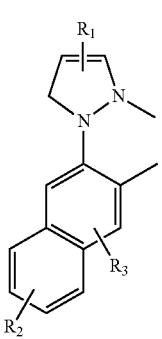
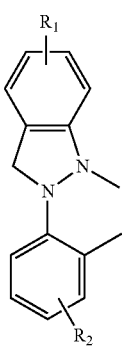
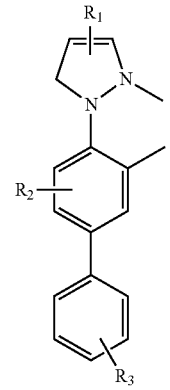
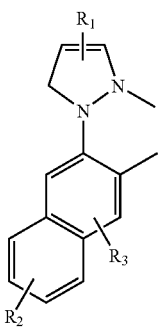
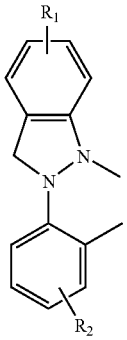
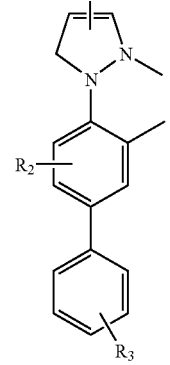

where Z is S, O, or $NR_8$, and $R_1$, $R_2$, $R_3$, $R_4$, $R_5$, $R_6$, $R_7$, and $R_8$ are each independently hydrogen, halogen, carboxylic acid alkyl ester, $CF_3$, CN, silyl, alkyl, aryl, alkoxy, aryloxy, amino, or arylene, wherein the aryl, the arylalkyl, and the alkoxy can be each independently substituted with halogen, $CF_3$, CN, silyl, alkyl, aryl, alkoxy, aryloxy, amino, or arylene, and adjacent Rs may be fused together to form a five- to seven-membered aliphatic or aromatic ring.

In the cyclometalated transition metal complex, the second mono anionic bidentate chelating ligand may be selected from ligands represented by formulae below:

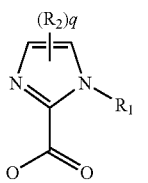
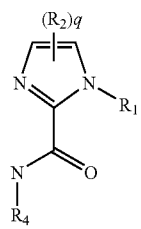
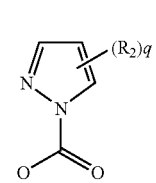
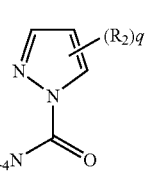
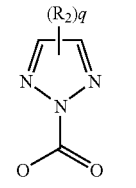
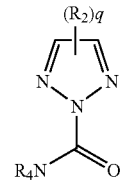

-continued

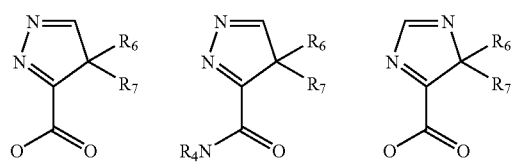
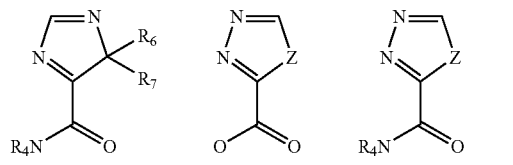
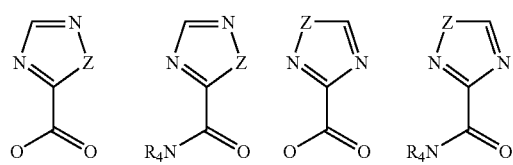
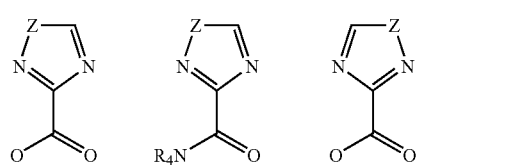
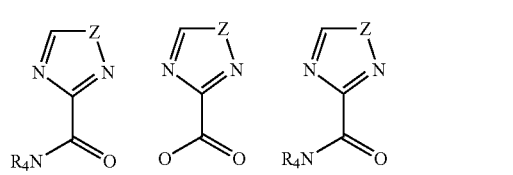
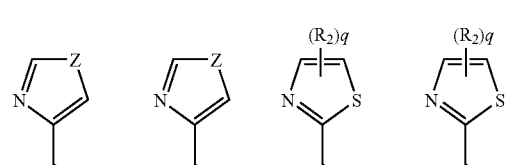
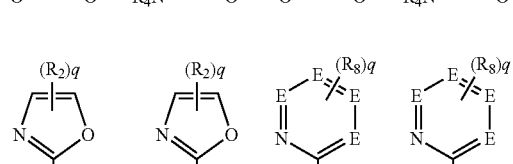
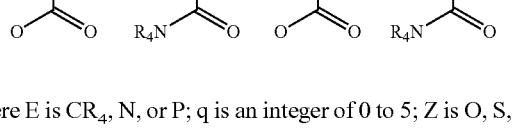
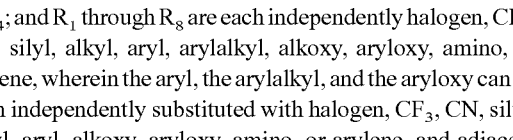
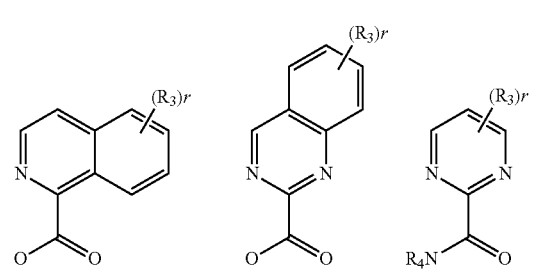

where E is $CR_4$, N, or P; q is an integer of 0 to 5; Z is O, S, or $NR_4$; and $R_1$ through $R_8$ are each independently halogen, $CF_3$, CN, silyl, alkyl, aryl, arylalkyl, alkoxy, aryloxy, amino, or arylene, wherein the aryl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five- to seven-membered aliphatic or aromatic ring.

In the cyclometalated transition metal complex, the second mono anionic bidentate chelating ligand may be selected from ligands represented by formulae below:

-continued

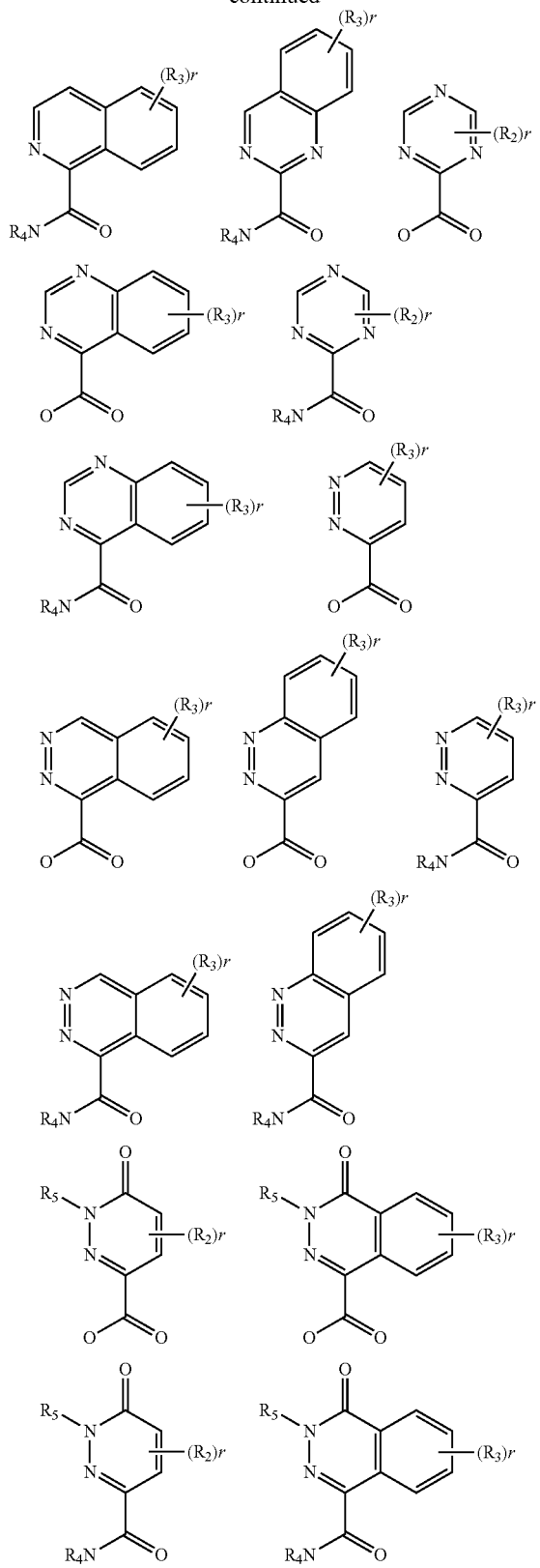

where r is an integer of 0 to 5, and $R_1$ through $R_8$ are each independently halogen, $CF_3$, CN, silyl, alkyl, aryl, arylalkyl, alkoxy, aryloxy, amino, or arylene, wherein the aryl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five- to seven-membered aliphatic or aromatic ring.

In the cyclometalated transition metal complex, the M can be Ru, Rh, Os, Ir, Pt, or Au.

In the cyclometalated transition metal complex, the M can be Ir.

In the cyclometalated transition metal complex, the transition compound of Formula 1 is a complex represented by one of formulae below:

<Formula 2>

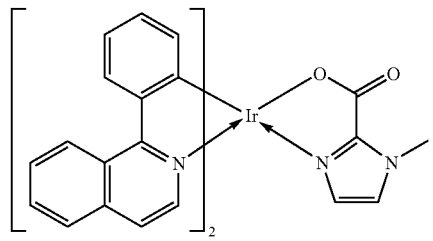

<Formula 3>

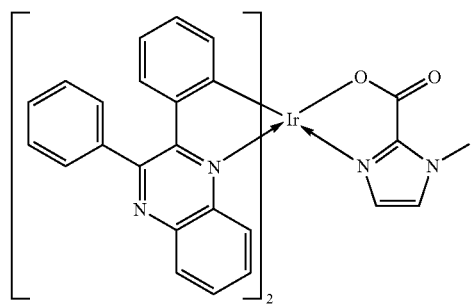

<Formula 4>

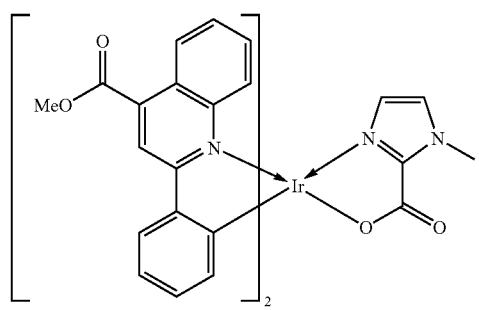

<Formula 5>

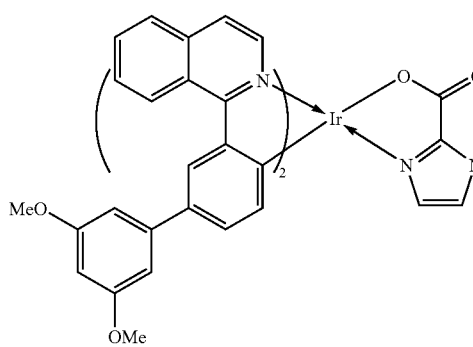

<Formula 6>
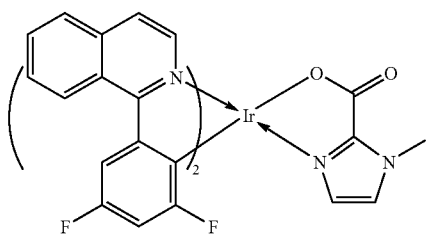

<Formula 7>
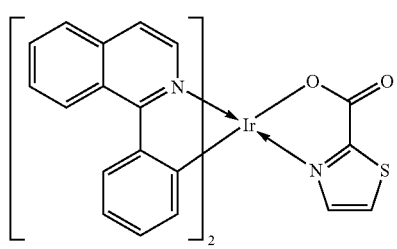

<Formula 8>
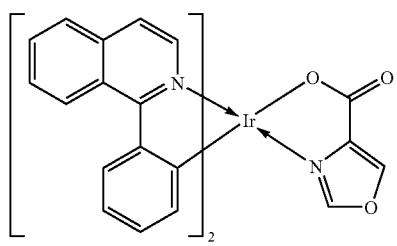

<Formula 9>
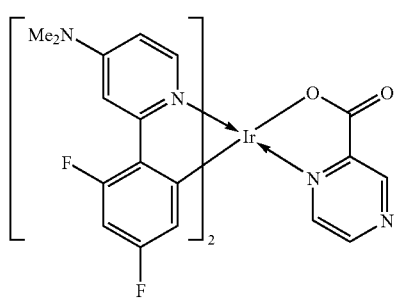

According to another aspect of the present invention, there is provided an organic light emitting device including an organic layer interposed between a pair of electrodes, the organic layer containing the cyclometalated transition metal complex.

The organic layer may further contain at least one material selected from the group consisting of one or more kinds of polymer hosts, a mixture of a polymer host and a low molecular weight host, a low molecular weight host, and a non-luminous polymer matrix.

The organic layer may further contain a green emission material or a blue emission material.

A cyclometalated transition metal complex according to the present invention includes a new ancillary ligand, thereby efficiently emit a red phosphor light through intersystem crossing (ISC) to triplets and then metal to ligand charge transfer (MLCT). An organic light emitting device manufactured using the transition metal complex shows higher luminous efficiency and higher external quantum efficiency than a conventional organic light emitting device in a red wavelength region.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
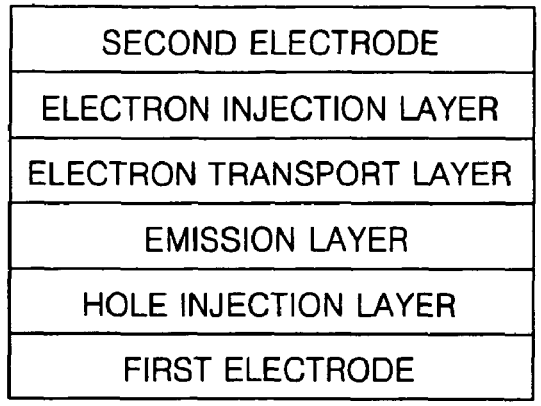
FIGS. 1A through 1C are sectional views of organic light emitting devices according to embodiments of the present invention.

The present invention will now be described more fully with reference to the accompanying drawings, in which exemplary embodiments of the invention are shown.

Hereinafter, the present invention will now be described in detail.

A cyclometalated transition metal complex according to an embodiment of the present invention is represented by Formula 1:

<Formula 1>
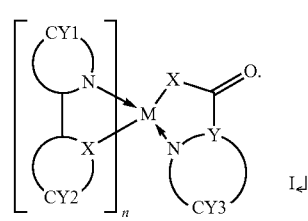

where M is a transition metal;

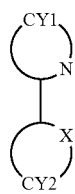

is a mono anionic bidentate chelating ligand (referred to as "a first mono anionic bidentate chelating ligand");

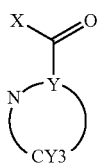

is a mono anionic bidentate chelating ligand (referred to as "a second mono anionic bidentate chelating ligand");

X and Y are each independently C, S, O, or N;

CY1, CY2, and CY3 are each independently aromatic or aliphatic rings; and n is 1 or 2.

In Formula 1, when X is N, N can be substituted with $R_4$ where $R_4$ is selected from group consisting of hydrogen, halogen, $CF_3$, CN, silyl, alkyl, aryl, alkoxy, aryloxy, amino, and arylene.

The cyclometalated transition metal complex of Formula 1 is a transition metal complex in which the first monoanionic bidentate chelating ligand acting as a primary ligand, and the second monoanionic bidentate chelating ligand acting as an ancillary ligand are coordinated. One of the features of the cyclometalated transition metal complex of Formula 1 is that a new ancillary ligand containing a carbonyl group,

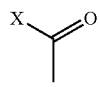

(where X is C, S, O, or N), connected to a hetero ring is coordinated therein. Since the new ancillary ligand is coordinated in the cyclometalated transition metal complex, an organic light emitting device manufactured using the cyclometalated transition metal complex shows higher photoluminescent quantum efficiency than organic light emitting devices manufactured using a conventional red fluorescent material or red phosphor material.

In the cyclometalated transition metal complex of Formula 1, the first mono anionic bidentate chelating ligand can be selected from ligands represented by formulae below:

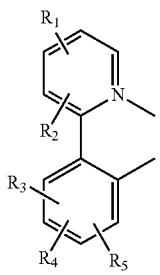
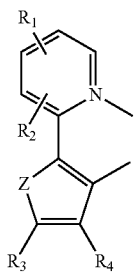

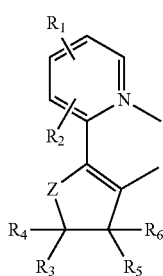
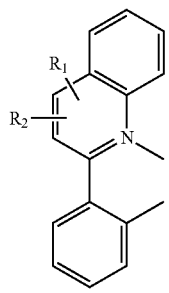

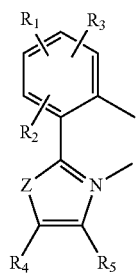
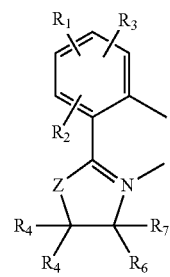

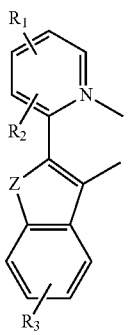
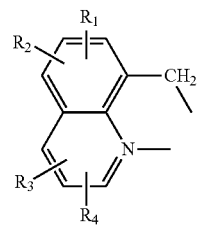

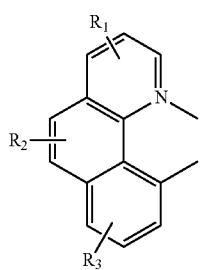
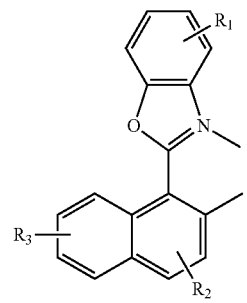

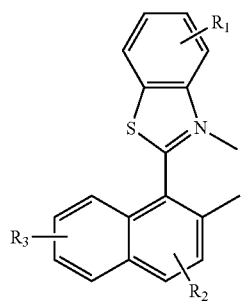
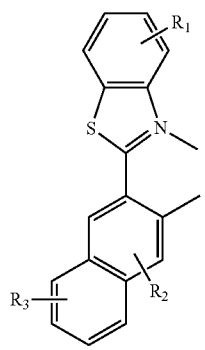

-continued

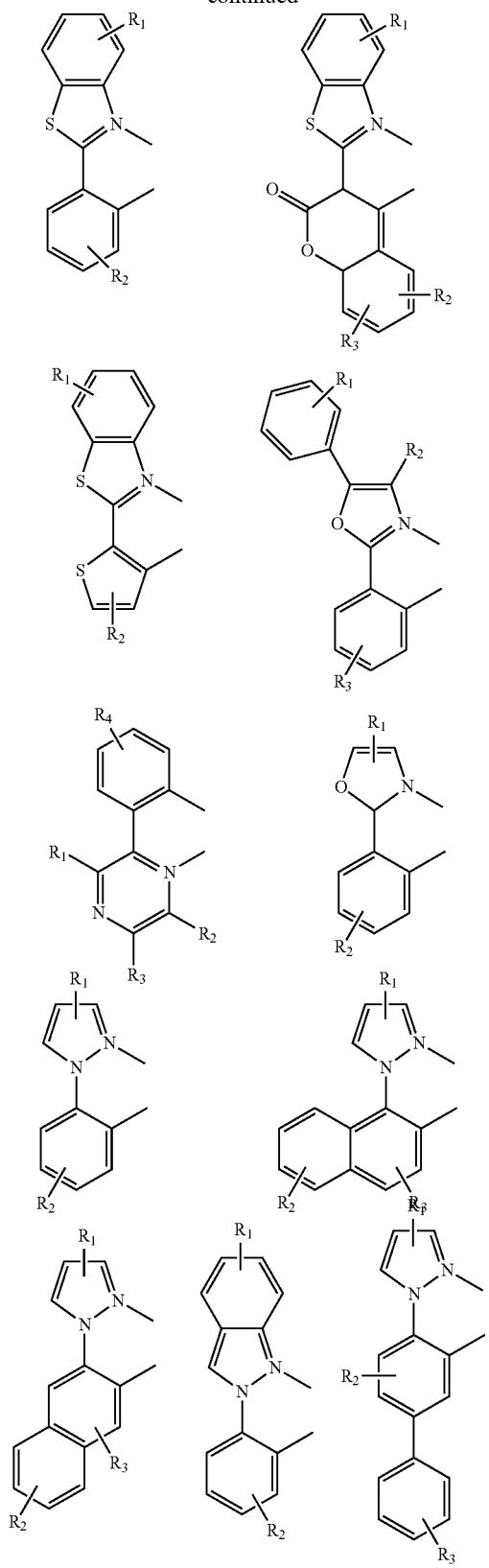

where Z is S, O, or NR$_8$, and
R$_1$, R$_2$, R$_3$, R$_4$, R$_5$, R$_6$, R$_7$, and R$_8$ are each independently hydrogen, halogen, carboxylic acid alkyl ester, CF$_3$, CN, silyl, alkyl, aryl, alkoxy, aryloxy, amino, or arylene, wherein the aryl, the arylalkyl, and the alkoxy can be each independently substituted with halogen, CF$_3$, CN, silyl, alkyl, aryl, alkoxy, aryloxy, amino, or arylene, and adjacent Rs may be fused together to form a five to seven membered aliphatic or aromatic ring.

In the cyclometalated transition metal complex of Formula 1, the second mono anionic bidentate chelating ligand can be selected from ligands represented by formulae below:

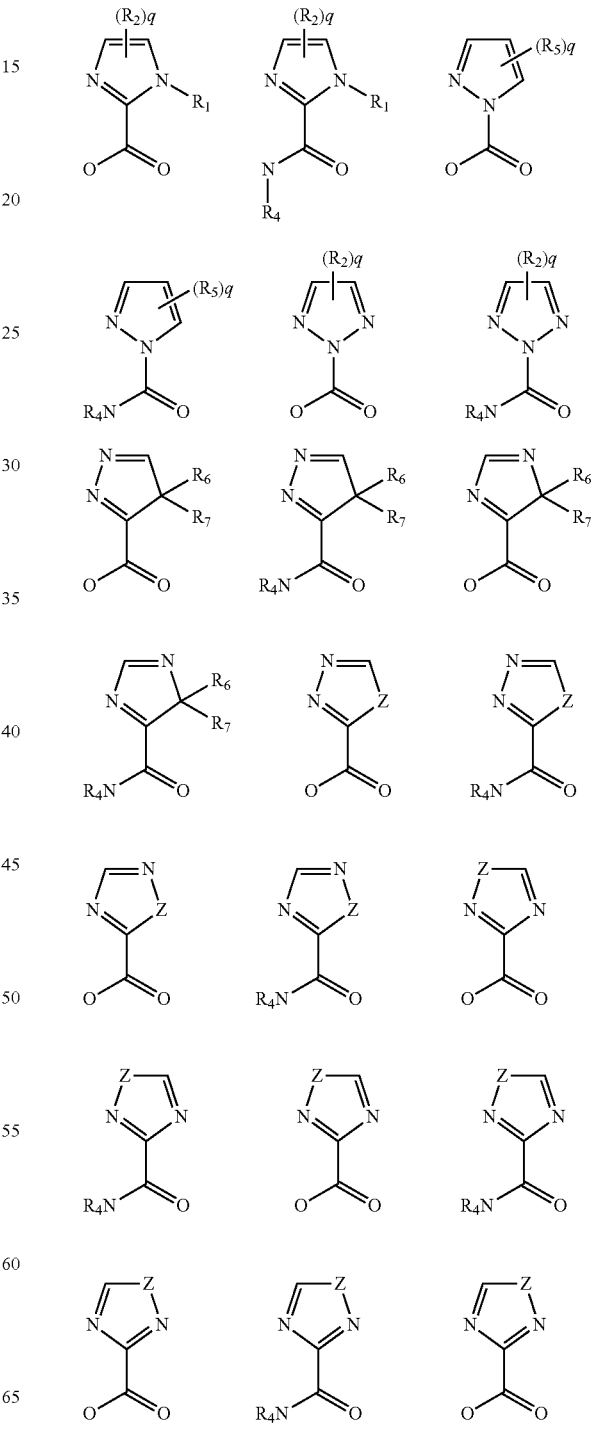

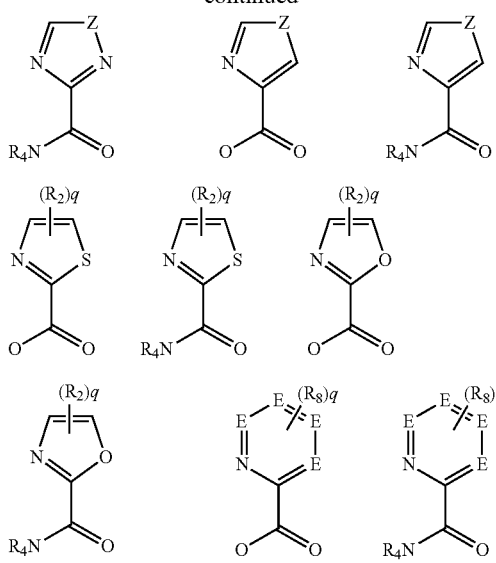

where E is $CR_4$, N, or P; q is an integer of 0 to 5; Z is O, S, or $NR_4$; and $R_1$ through $R_8$ are each independently halogen, $CF_3$, CN, silyl, alkyl, aryl, arylalkyl, alkoxy, aryloxy, amino, or arylene, wherein the aryl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five to seven membered aliphatic or aromatic ring.

Particularly, the second mono anionic bidentate chelating ligand can be selected from ligands represented by formulae below:

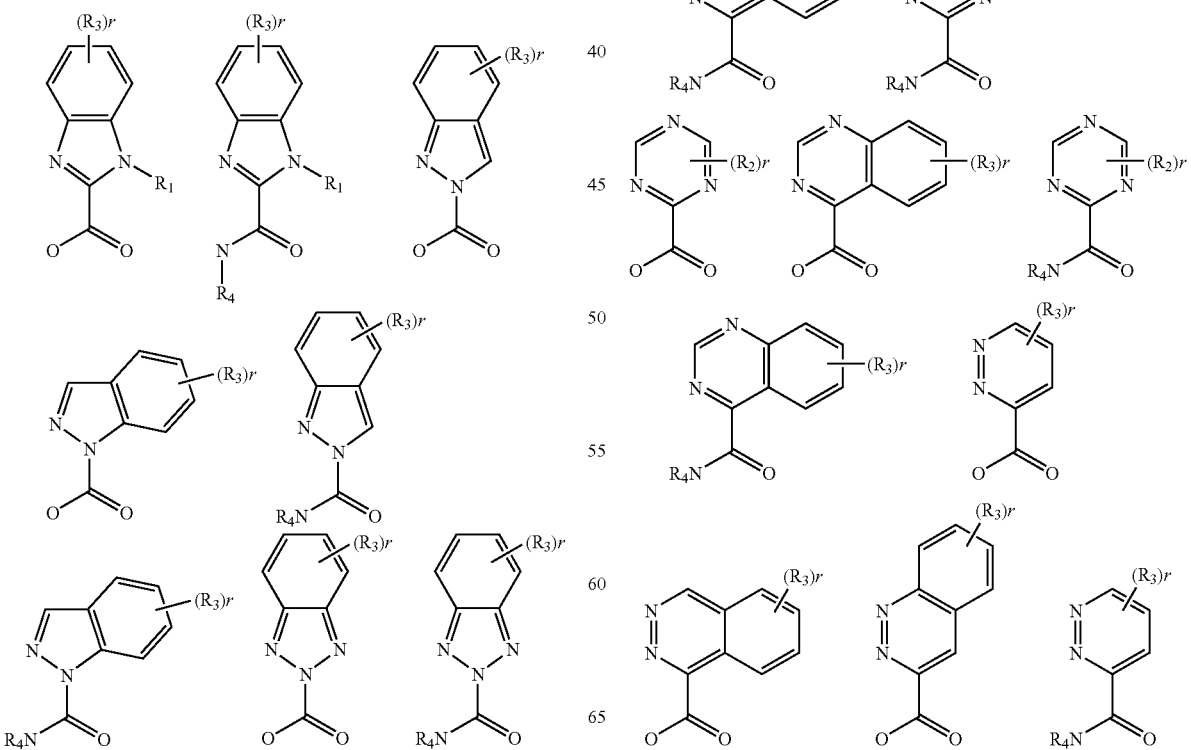
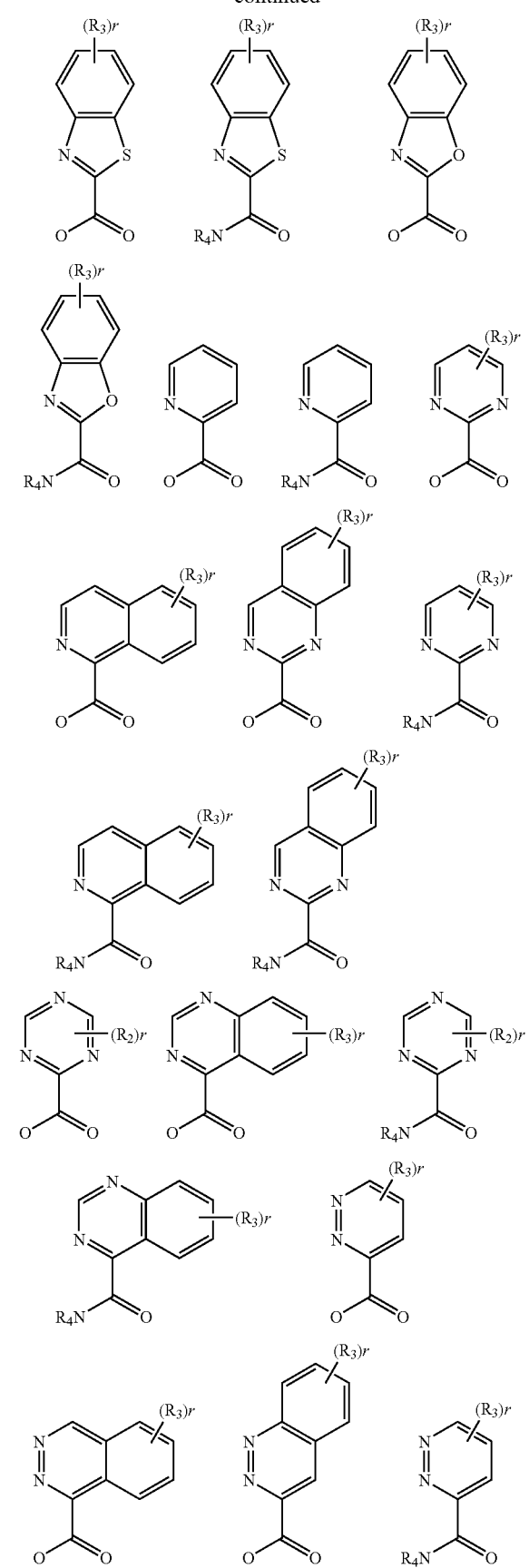

-continued

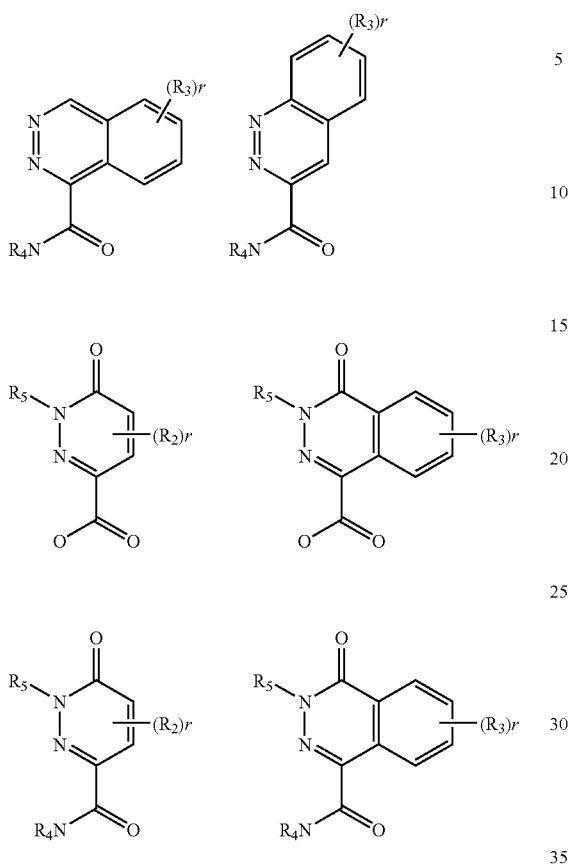

where r is an integer of 0 to 5, and $R_1$ through $R_8$ are each independently halogen, $CF_3$, CN, silyl, alkyl, aryl, arylalkyl, alkoxy, aryloxy, amino, or arylene, wherein the alkyl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five to seven membered aliphatic or aromatic ring.

In the cyclometalated transition metal complex, M may be Ru, Rh, Os, Ir, Pt, or Au.

Preferably, M is Ir.

The cyclometalated transition metal complex of Formula 1 can be a complex represented by one of formulae below:

<Formula 2>

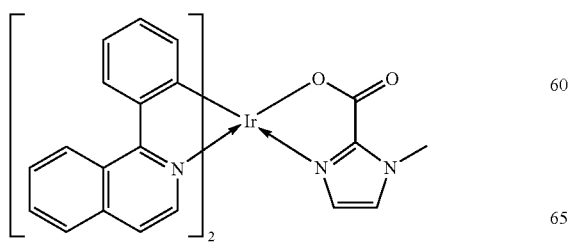

-continued

<Formula 3>

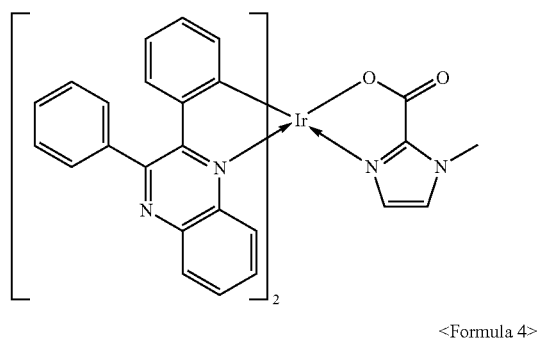

<Formula 4>

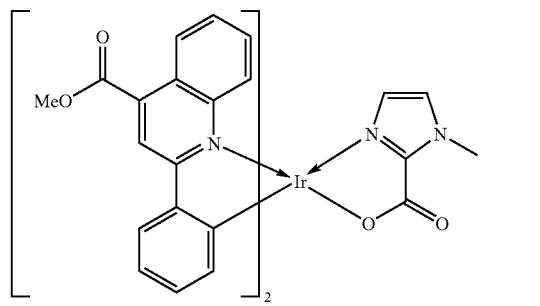

<Formula 5>

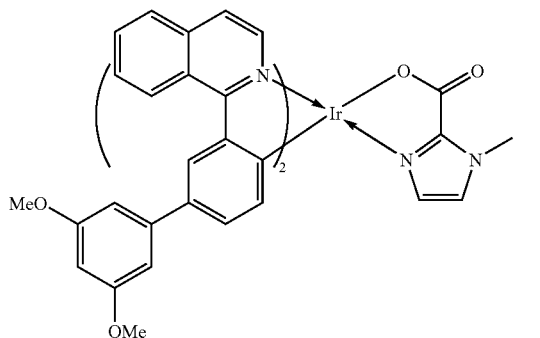

<Formula 6>

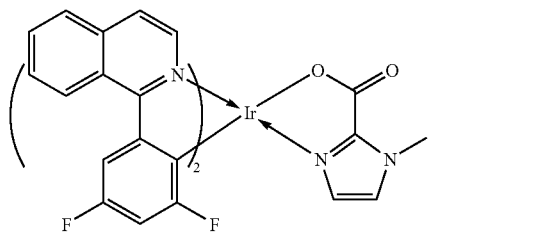

<Formula 7>

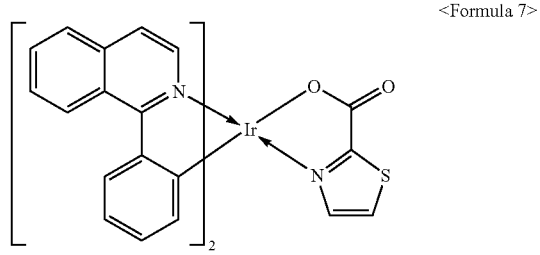

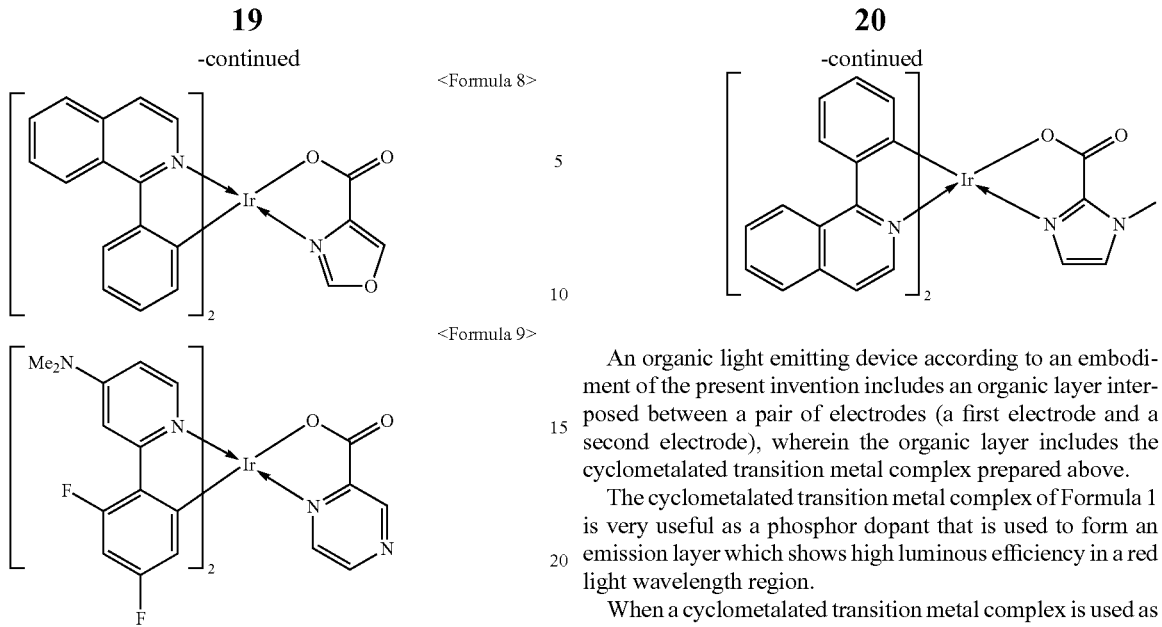

In Formulae 2 through 9, respective ligands can be substituted with halogen, $CF_3$, CN, silyl, alkyl, aryl, alkoxy, aryloxy, amino, or arylene.

The cyclometalated transition metal complex according to embodiment of the present invention emits light of a wavelength of between 500 nm and 670 nm.

The cyclometalated transition metal complexes according to embodiments of the present invention can be prepared using various methods. For example, when M is Ir, a [Ir(CY1)(CY2)Cl]$_2$ derivative can be used as a starting material in a method developed by Watts group (*Inorg. Chem.* 1998, 27, 3464-3471) to prepare a cyclometalated transition metal complex.

Hereinafter, a process of synthesizing a transition metal complex containing a 2-methylimidazole-1-carboxylate ligand that is an example of the cyclometalated transition metal complex of Formula 1 according to an embodiment of the present invention will be described.

Referring to Reaction Scheme 1, a [Ir(CY1)(CY2)Cl]$_2$ derivative and 1-methylimidazole-2-carboxylate lithium salt are mixed with a chloroform solvent, and then stirred at a temperature of 30-50° C. for 18 hours. As a result, a cyclometalated transition metal complex according to an embodiment of the present invention can be synthesized.

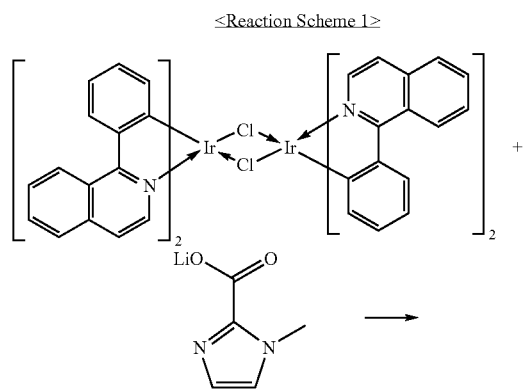

<Reaction Scheme 1>

An organic light emitting device according to an embodiment of the present invention includes an organic layer interposed between a pair of electrodes (a first electrode and a second electrode), wherein the organic layer includes the cyclometalated transition metal complex prepared above.

The cyclometalated transition metal complex of Formula 1 is very useful as a phosphor dopant that is used to form an emission layer which shows high luminous efficiency in a red light wavelength region.

When a cyclometalated transition metal complex is used as a phosphor dopant in an organic light emitting device, the organic layer may further include at least one material selected from one or more kinds of polymer host, a mixture of a polymer host and a low molecular weight host, a low molecular weight host, and a non-emission polymer matrix.

The polymer host, the low molecular weight host, and the non-emission polymer matrix can be any polymer host, any low molecular weight host, and any non-emission polymer matrix that are commonly used in an emission layer of an organic light emitting device. Examples of the polymer host are PVK(polyvinylcarbazole), polyfluorene etc. Examples of the low molecular weight host are CBP(4,4'-N,N'-dicarbazole-biphenyl), 4,4'-bis[9-(3,6-biphenylcarbazolyl)]-1,1'-biphenyl, 9,10-bis[(2',7'-t-butyl)-9',9"-spirobifluorenylanthracene, tetrafluorene, etc. Examples of the non-emission polymer matrix are polymethylmethacrylate, polystyrene, etc. However, the polymer host, the molecular weight host, and the non-emission matrix are not limited thereto.

The content of the transition metal complex may be in the range of 1-30 parts by weight based on 100 parts by weight of the total weight of material used to form an emission layer. The transition metal complex can be used to form an emission layer by vacuum depositing, sputtering, printing, coating, injecting, electron beaming, or the like.

In the organic light emitting device, the organic layer may further include a green light emitting material or a blue light emitting material. When the organic layer further contains both green and blue light emitting materials, white light can be obtained.

The thickness of the organic layer may be in a range of 10-1,000 nm. The organic layer refers to a layer formed of an organic material interposed between a pair of electrodes of an organic light emitting device. Such layer can be, in addition to an emission layer, an electron transport layer, a hole transport layer, etc.

The organic light emitting device according to an embodiment of the present invention can be manufactured according to a conventional process of manufacturing an organic light emitting device without the need for special apparatuses and methods.

The organic light emitting device may have various structures according to embodiments of the present invention. The organic light emitting device can further include at least one layer selected from a buffer layer, a hole injection layer, a hole transport layer, an electron blocking layer, a hole blocking layer, an electron transport layer, and an electron injection layer, interposed between a pair of electrodes.

Figure 1B:
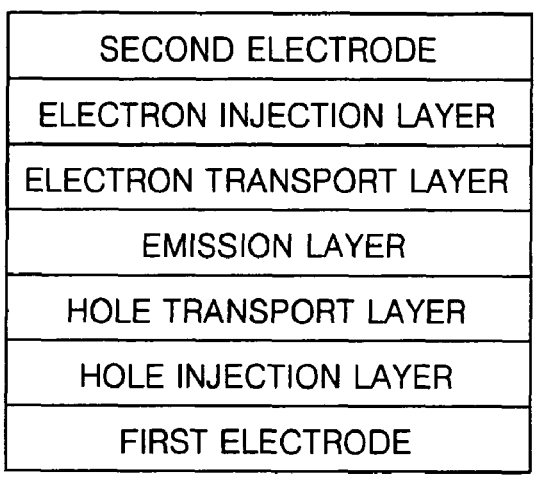
Figure 1C:
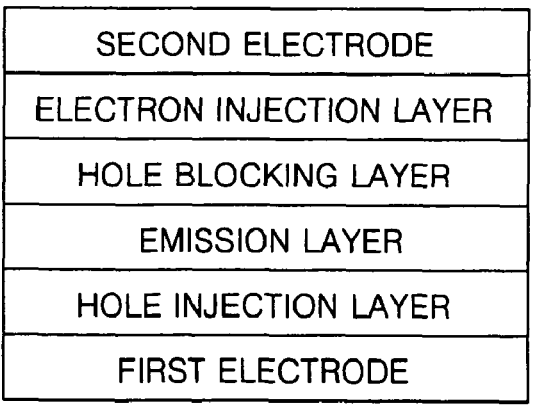

Organic light emitting devices according to embodiments of the present invention are illustrated in FIGS. 1A, 1B, and 1C. FIG. 1A is a sectional view of an organic light emitting device that includes a first electrode/hole injection layer/emission layer/electron transport layer/electron injection layer/second electrode structure. FIG. 1B is a sectional view of an organic light emitting device that includes a first electrode/hole injection layer/hole transport layer/emission layer/electron transport layer/electron injection layer/second electrode structure. FIG. 1C is a sectional view of an organic light emitting device that includes a first electrode/hole injection layer/emission layer/hole blocking layer/electron injection layer/second electrode structure. In these organic light emitting devices, the emission layer can include the transition metal complex according to an embodiment of the present invention. The emission layer of an organic light emitting device according to an embodiment of the present invention can include a phosphor or fluorescent dopant of green, blue, or white.

Hereinafter, a method of manufacturing an organic light emitting device according to an embodiment of the present invention will be described in detail with reference to the organic light emitting device illustrated in FIG. 1C.

First, a large work function material that is used to form a first electrode is deposited or sputtered on a substrate to form a first electrode. The first electrode can act as an anode. The substrate can be any substrate that is used in a conventional organic light emitting device. For example, the substrate can be a glass substrate or a transparent plastic substrate, both of which have excellent mechanical strength, thermal stability, transparency, and surface smoothness, can be easily handled, and are waterproof. A material that is used to from the first electrode can be a transparent, conductive metal, such as Indium tin oxide (ITO), Indium zinc oxide (IZO), tin oxide ($SnO_2$), zinc oxide (ZnO), and the like.

Then, a hole injection layer (HIL) can be formed on the first electrode by vacuum deposition, spin coating, casting, Langmuir-Blodgett (LB), or the like.

When the HIL is formed by vacuum deposition, deposition conditions may vary according to a material that is used to form the HIL and desired structural and thermal properties of a HIL that is to be formed. In general, however, the deposition temperature may be in the range of 100-500° C., a degree of vacuum may be in the range of $10^{-8}$-$10^{-3}$ torr, a vacuum deposition speed may be in the range of 0.01-100 Å/sec, and a thickness of the HIL may be in the range of 10 Å-5 μm.

When the HIL is formed by spin coating, coating conditions may vary according to a material that is used to form the HIL and desired structural and thermal properties of the HIL that is to be formed. In general, however, a coating speed may be in the range of about 2,000 rpm-5,000 rpm, and a temperature for a heat treatment that is performed to remove a used solvent after coating may be in the range of about 80° C.-200° C.

A material that is used to form the HIL is not limited, and can be a phthalocyanine compound, such as copper phthalocyanine disclosed in U.S. Pat. Publication No. 4,356,429; a starburst type amine derivative, such as TCTA, m-MTDATA, or m-MTDAPB, disclosed in Advanced Material, 6, p. 677 (1994); or a soluble conductive polymer such as Pani/DBSA (polyaniline/dodecylbenzenesulfonic acid) PEDOT/PSS (poly(3,4-ethylenedioxythiophene)/poly(4-styrenesulfonate), Pani/CSA (polyaniline/camphor sulfonic acid), or PANI/PSS (polyaniline)/poly(4-styrenesulfonate).

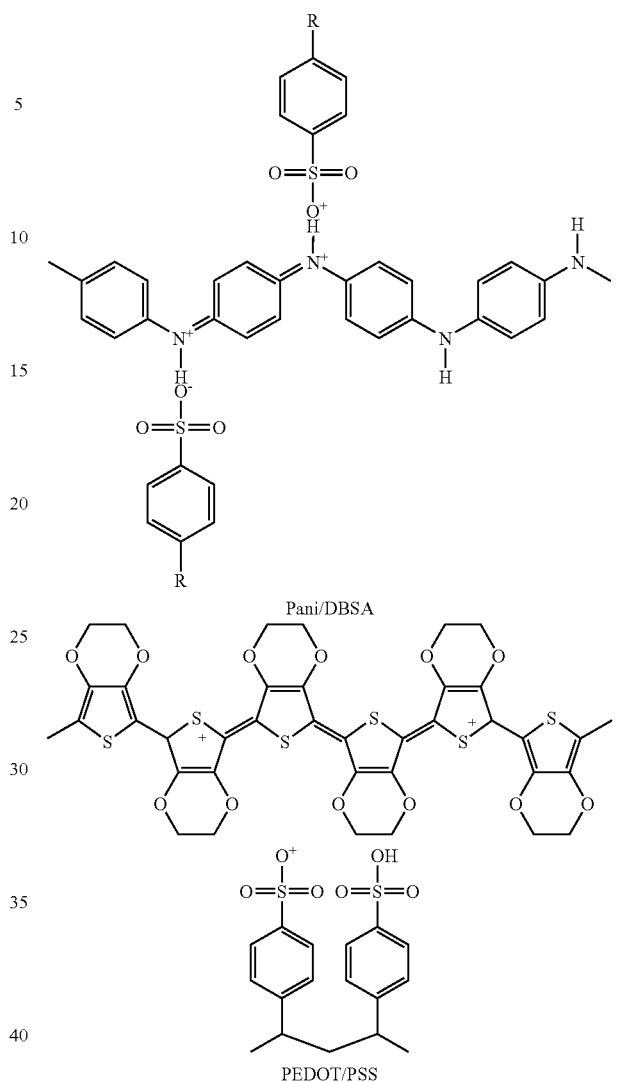

Pani/DBSA

PEDOT/PSS

A thickness of the HIL may be in the range of about 100 Å-10,000 Å, preferably 100 Å-1,000 Å. When the thickness of the HIL is less than 100 Å, hole injection properties may decrease. On the other hand, when the thickness of the HIL is more than 10,000 Å, the operating voltage of the device may increase.

Then, an emission layer (EML) can be formed on the HIL by vacuum depositing, spin coating, casting, LB, or the like. When the EML is formed by vacuum depositing or spin coating, formation conditions may vary according to a material that is used to form the EML. In general, however, the EML may be formed under similar conditions as for the HIL.

The EML can be formed using an arylene-based derivative having a polar functional group of Formula 1 as described above. At this time, a soluble compound can be used together with an organic semiconductor. The organic semiconductor can be pentacene, polythiophene, tetrathiafulvalene, or the like.

The arylene-based derivative of Formula 1 can be used with an appropriate host material that is known in the art. The host material can be $Alq_3$, CBP(4,4'-N,N'-dicarbazole-biphenyl), PVK(poly(n-vinylcarbazole)), or the like.

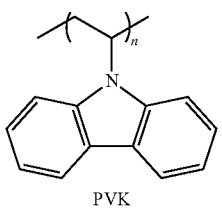

PVK

There are various dopants that are known that can be used to form the EML, in addition to an aminostyryl compound used in the present invention. For example, a fluorescent dopant used in the EML can be IDE102 or IDE105 that is commercially available from Idemitsu Inc, and C545T that is commercially available from Hayashibara Inc., and a phosphor dopant used in the EML can be PtOEP that is a red phosphor dopant, RD 61 that is available from UDC Inc., Ir(PPy)$_3$(PPy=2-phenylpyridine) that is a green phosphor dopant, F2Irpic that is a blue phosphor dopant, RD 61 that is a red phosphor dopant available from UDC Inc., or the like.

A concentration of the dopant is not limited, and may be in the range of 0.01 to 15 parts by weight based on 100 parts by weight of a host.

The thickness of the emission layer may be in the range of about 100 Å-1,000 Å, preferably 200 Å-600 Å. When the thickness of the emission layer is less than 100 Å, the luminous efficiency may decrease. On the other hand, when the thickness of the emission layer is more than 1,000 Å, the operating voltage may increase.

When the EML is formed using a phosphor dopant, a hole blocking layer (HBL) can be formed on the EML to prevent diffusion of triplet excitons or holes into an electron injection layer by vacuum deposition, spin coating, casting, LB, or the like. When the HBL is formed by vacuum deposition or spin coating, formation conditions may vary according to a compound that is used to form the HBL. In general, however, the HBL can be formed under similar conditions as when the HIL is formed. A known material that is used to form the HBL can be an oxadiazole derivative, a triazole derivative, phenanthroline derivative, or BCP (2,9-dimethyl-4,7-diphenyl-1,10-phenanthroline) disclosed in JP 11-329734(A1) as a hole blocking material.

A thickness of the HBL may be in the range of 50 Å-1,000 Å, preferably 100 Å-300 Å. When the thickness of the HBL is less than 50 Å, hole blocking properties may decrease. On the other hand, when the thickness of the HBL is more than 1,000 Å, the operating voltage of the device may increase.

A material that allows electrons to be easily injected from the anode can be deposited on the HBL to form an electron injection layer (EIL), and is not limited.

The EIL can be formed using a known material that is used to form a conventional EIL, such as LiF, NaCl, CsF, Li$_2$O, Ba, or the like. Formation conditions for the EIL may vary according to a material that is used to form EIL. In general, however, the EIL can be formed under similar conditions as when the HIL is formed.

A thickness of the EIL may be in the range of about 1 Å-100 Å, preferably 5 Å-50 Å. When the thickness of the EIL is less than 1 Å, the electron injection property may decrease. On the other hand, when the thickness of the EIL is more than 100 Å, the operating voltage of the device may increase.

Then, a second electrode can be formed on the EIL by vacuum depositing or sputtering. The second electrode can act as a cathode. A metal that is used to form the second electrode may be a low work function metal, an alloy, an electrically conductive compound, or a mixture of these. For example, the metal that is used to form the second electrode can be Li, Mg, Al, Al—Li, Ca, Mg—In, Mg—Ag, or the like.

Meanwhile, in order to obtain a top emission type display device, a transparent cathode formed of ITO or IZO can be used.

Organic light emitting devices according to embodiments of the present invention can have various structures, in addition to the first electrode/hole injection layer(HIL)/emission layer (EML)/hole blocking layer (HBL)/electron injection layer/second electrode structure illustrated in FIG. 1C. In addition, these layers may not be used when not needed.

For example, a buffer layer, a hole transport layer, and an electron transport layer (ETL) can be further added.

A material that is used to form a buffer layer can be any material that is commercially used, and can be copper phthalocyanine, polythiophene, polyaniline, polyacetylene, polypyrrole, polyphenylenevinylene, or derivatives of these. However, the material that is used to form a buffer layer is not limited thereto.

A hole transport layer (HTL) can be formed on the HIL by vacuum depositing, spin coating, casting, LB, or the like. When the HTL is formed by vacuum depositing or spin coating, deposition conditions and coating conditions may vary according to a material that is used to from the HTL. In general, however, the HTL can be formed under similar conditions as when the HIL is formed.

A material that can be used to form the HTL is not limited, and can be any known material that is conventionally used to form a HTL. For example, a material that can be used to form the HTL is a carbazole derivative, such as N-phenylcarbazole or polyvinylcarbazole, an amine derivative having an aromatic condensation ring, such as N,N'-bis(3-methylphenyl)-N,N'-diphenyl-[1,1-biphenyl]-4,4'-diamine(TPD), N,N'-di(naphthalene-1-yl)-N,N'-diphenyl benzidine (α-NPD), or the like.

A thickness of the HTL may be in the range of about 50 Å-1,000 Å, preferably 100 Å-600 Å. When the thickness of the HTL is less than 50 Å, the hole transporting property may decrease. On the other hand, when the thickness of the HTL is more than 1,000 Å, the operating voltage of the device may increase.

The ETL can be formed by vacuum depositing, spin coating, casting, or the like. When the ETL is formed by vacuum depositing or spin coating, formation conditions may vary according to a material that is used to form an ETL. In general, however, the ETL can be formed under similar conditions as when the HIL is formed. The material that is used to form the ETL stably transports electrons injected from an electron injection electrode (cathode), and can be polyoxadiazole, a quinoline derivative, such as tris(8-quinolinolate) aluminum (Alq$_3$), TAZ, or the like.

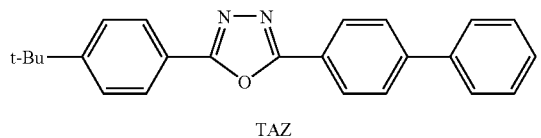

TAZ

A thickness of the ETL may be in the range of about 100 Å-1,000 Å, preferably 200 Å-500 Å. When the thickness of the ETL is less than 100 Å, the electron transport property may decrease. On the other hand, when the thickness of the ETL is more than 1,000 Å, the operating voltage of the device may increase.

A cyclometalated transition metal complex according to an embodiment of the present invention can emit light having a wavelength of between 500 and 670 nm. Emission diodes using such an organic metal complex can be used in a light source illumination for full-color display, back light, billboards, optical communication, interior decorations, or the like.

The cyclometalated transition metal complexes of Formula 1 and Formulae 2 through 9 are prepared using a conventional organic synthesis method. The compounds synthesized were identified using 1H NMR and a Mass spectrometer.

Hereinafter, Complexes 2 through 11 respectively represented by Formulae 2 through 11 (hereinafter, referred to as Complex 2 through Complex 11) will be described as prepared according to Synthesis Examples and Examples, but the present invention is not limited to these Synthesis Examples and Examples. Compounds are respectively represented by formulae having the same number.

SYNTHESIS EXAMPLES

Synthesis Example 1

Synthesis of Piq(phenylisoquinoline)dimer

<Reaction Scheme 2>

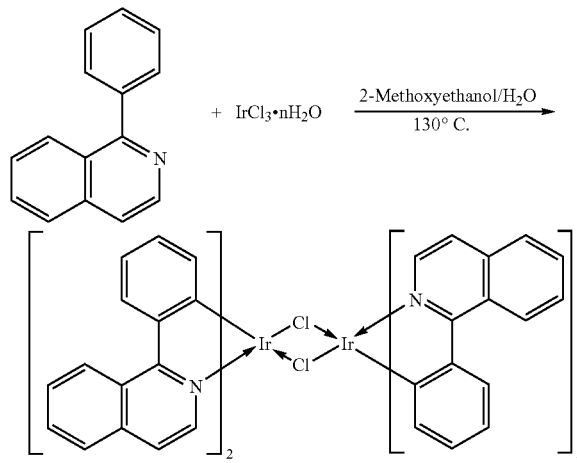

Piq dimer ([Ir(Piq)₂Cl]₂) that is red powder was synthesized using 2-phenylisoquinoline ligand and IrCl₃.nH₂O. The synthesis method disclosed in J. Am. Chem. Soc., 1984, 106, 6647-6653 which is incorporated herein by reference was used.

Synthesis Example 2

Synthesis of 2,3-diphenylquinoxaline (DPQX) dimer

<Reaction Scheme 3>

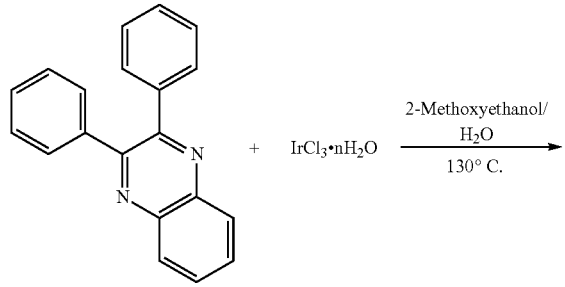

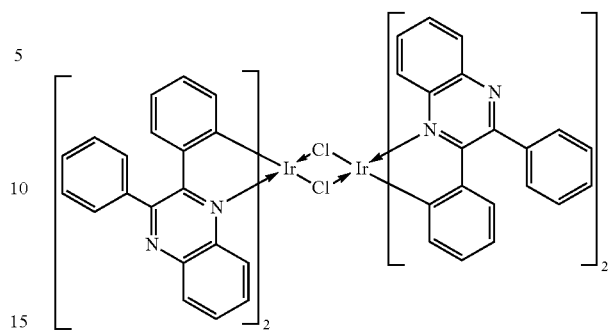

2,3-diphenylquinoxaline dimer ([Ir(DPQX)₂Cl]₂) was synthesized in the same manner as in Synthesis Example 1, except that 2,3-diphenylquinoxaline was used instead of 2-phenylisoquinoline.

Synthesis Example 3

Synthesis of methyl 2-phenyl-4-quinolinecarboxylate (MPQC) dimer

<Reaction Scheme 4>

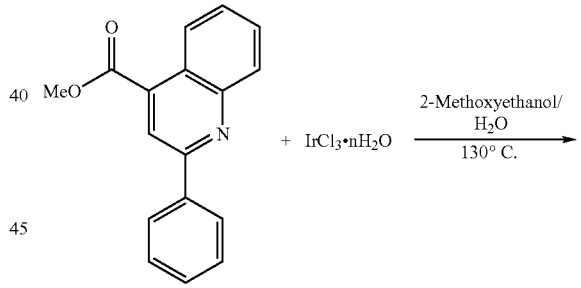

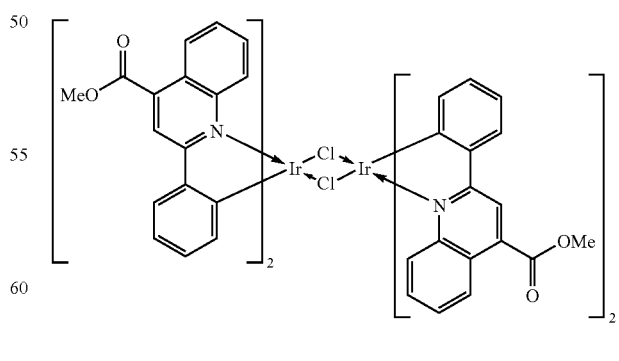

Methyl 2-phenyl-4-quinolinecarboxylate dimer ([Ir(MPQC)₂Cl]₂) was synthesized in the same manner as in Synthesis Example 1, except that methyl 2-phenyl-4-quinolinecarboxylate was used instead of 2-phenylisoquinoline.

Synthesis Example 4

Synthesis of 2-[3-(3,5-dimetoxyphenyl)phenyl]isoquinoline (DMPPiq) dimer

<Reaction Scheme 5>

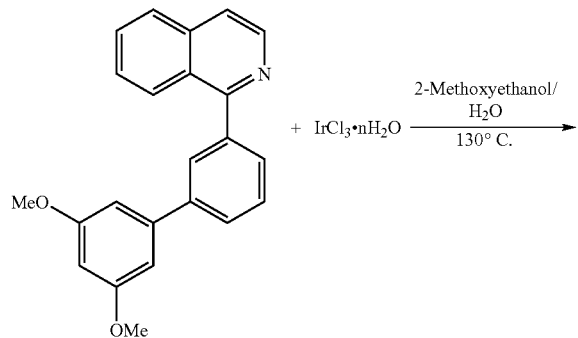

2-[3-(3,5-dimetoxyphenyl)phenyl]-isoquinoline dimer ([Ir(DMPPiq)$_2$Cl]$_2$) was synthesized in the same manner as in Synthesis Example 1, except that -[3-(3,5-dimetoxyphenyl)phenyl]-isoquinoline was used instead of 2-phenylisoquinoline.

Synthesis Example 5

2-(3,5-difluorophenyl)-isoquinoline (F2Piq) dimer

<Reaction Scheme 6>

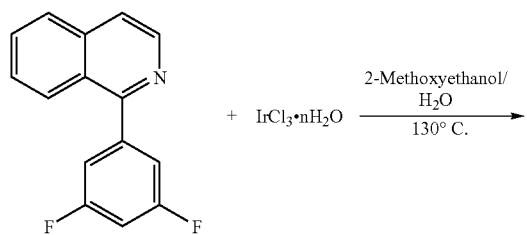

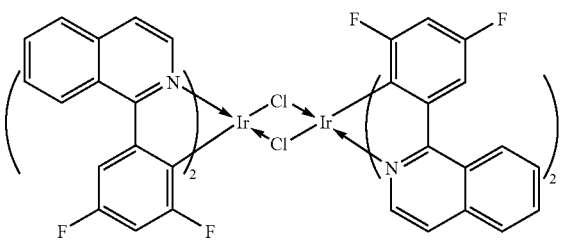

2-(3,5-difluorophenyl)-isoquinoline dimer ([Ir(F$_2$Piq)$_2$Cl]$_2$) was synthesized in the same manner as in Synthesis Example 1, except that 2-(3,5-difluorophenyl)-isoquinoline was used instead of 2-phenylisoquinoline.

Synthesis Example 6

Synthesis of (DMAF$_2$ppy) dimer

<Reaction Scheme 7>

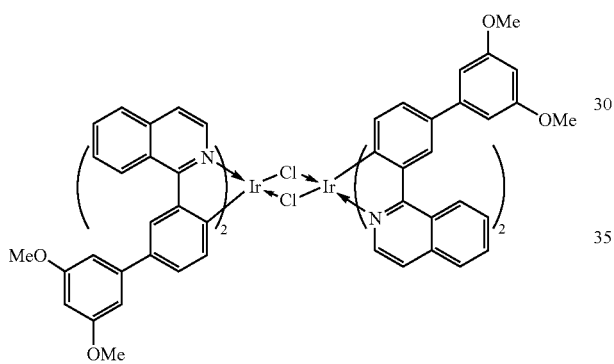

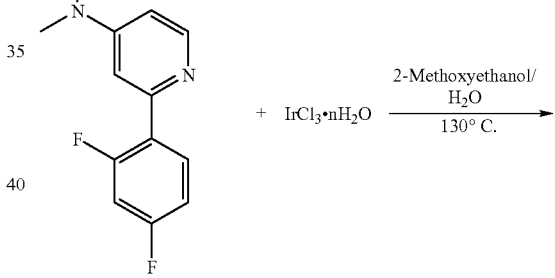

DMAF$_2$ppy Dimer 2-(2,4-difluorophenyl)-(4-dimethylamino)pyridine dimer ([Ir(DMAF2PPy)$_2$Cl]$_2$) was synthesized in the same manner as in Synthesis Example 1, except that 2-(2,4-difluorophenyl)-(4-dimethylamino)pyridine was used instead of 2-phenylisoquinoline.

EXAMPLE

Example 1

Synthesis of Complex 2 represented by Formula 2

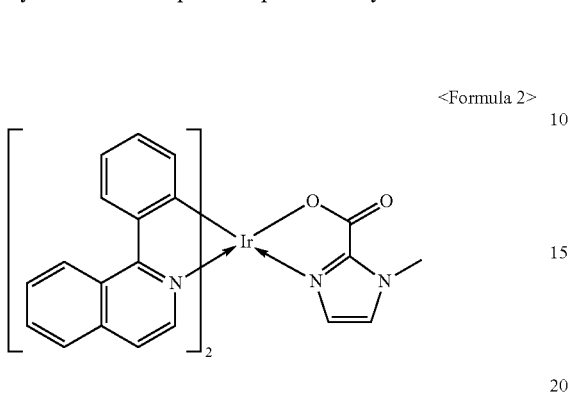

<Formula 2>

Figure 2:
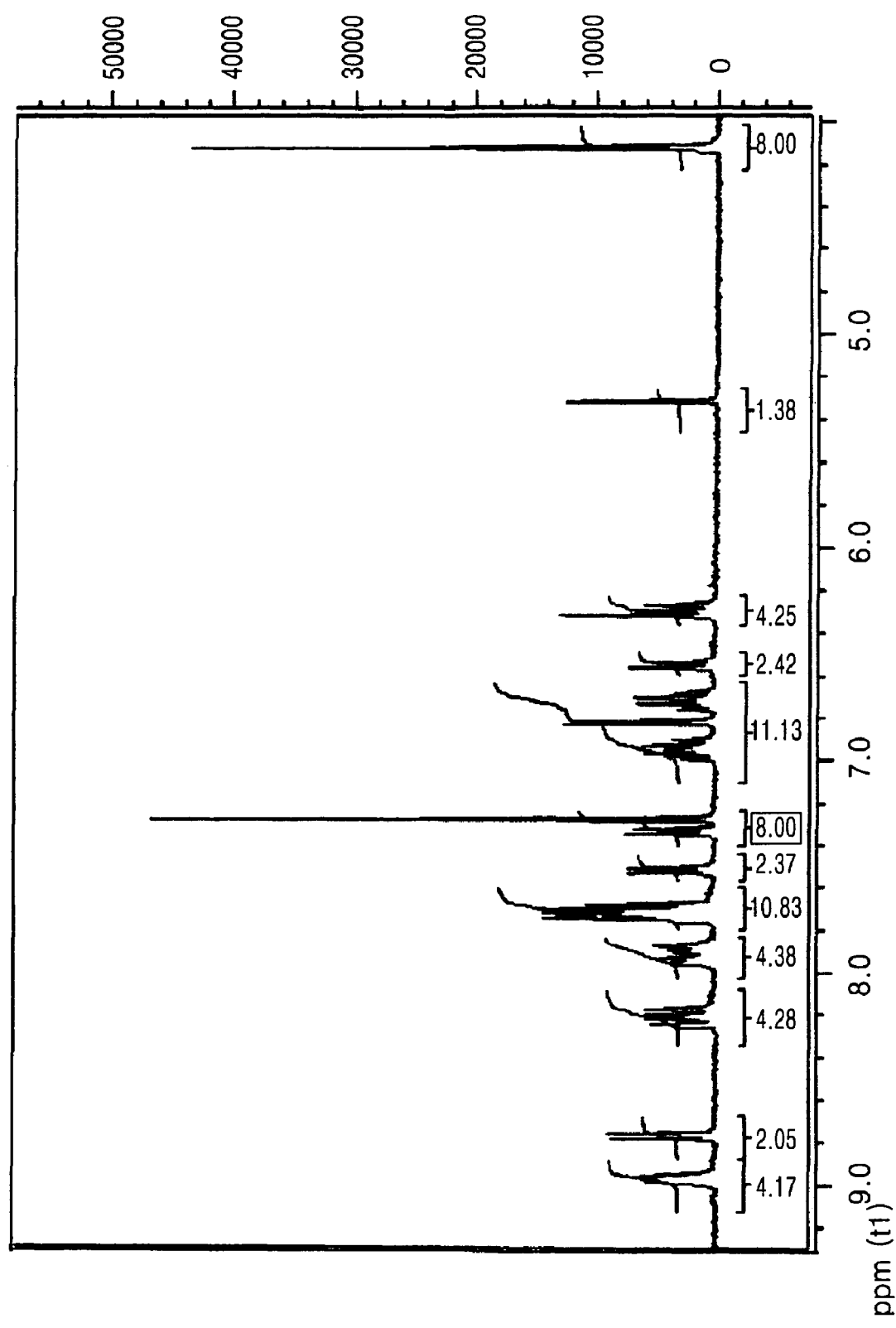
FIG. 2 is a graph showing results of a $^1$H NMR test of Complex 2 according to an embodiment of the present invention.
Figure 3:
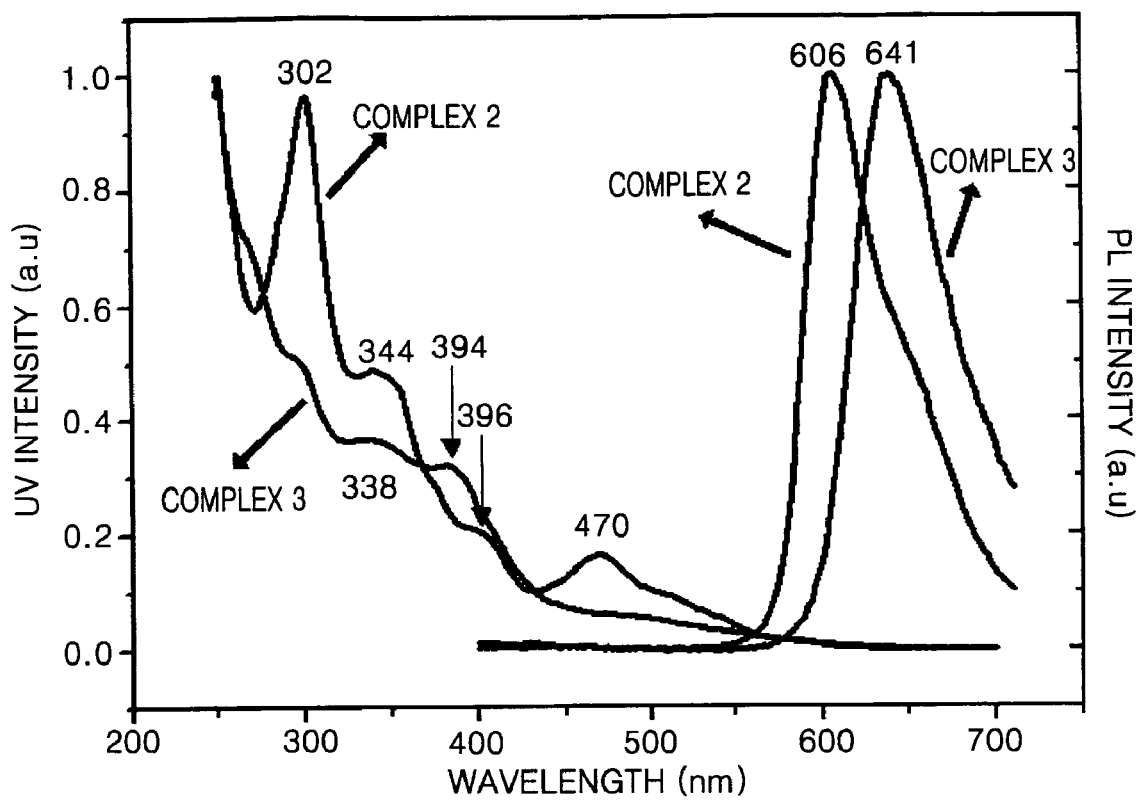
FIG. 3 is a graph showing results of UV and PL tests of Complexes 2 and 3 according to embodiments of the present invention.
Figure 4:
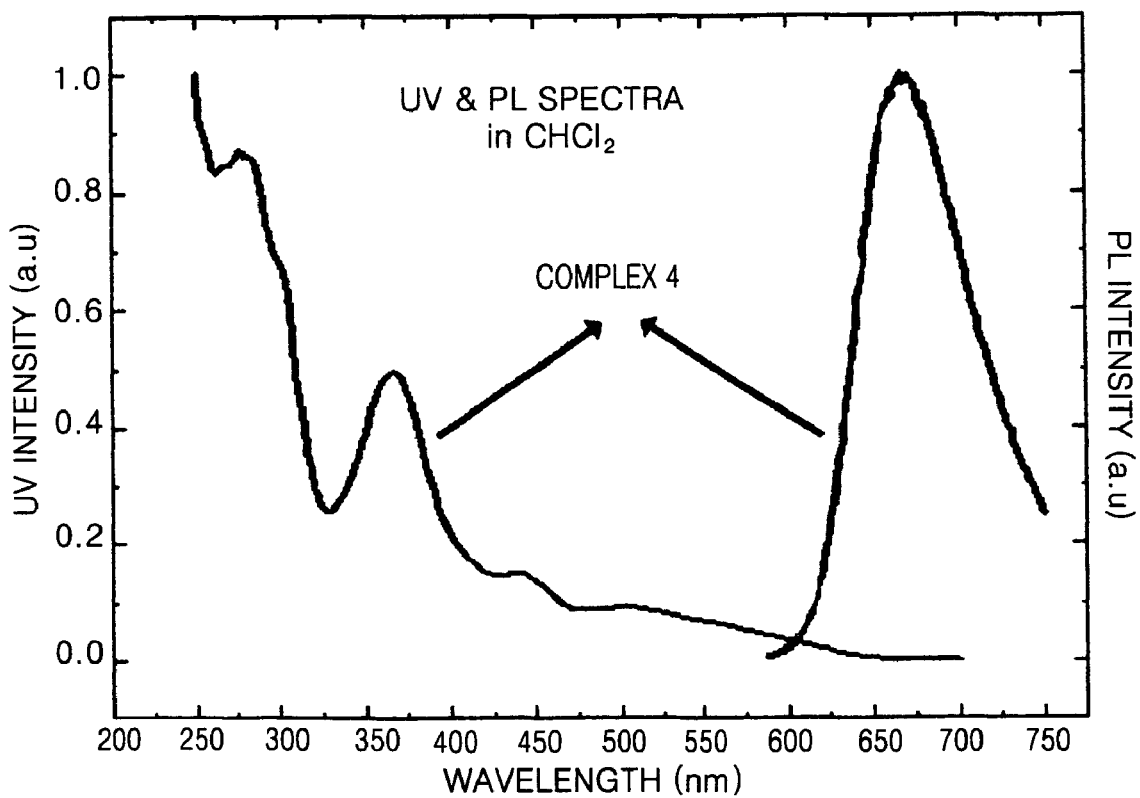
FIG. 4 is a graph showing results of UV and PL tests of Complex 4 according to an embodiment of the present invention.
Figure 5:
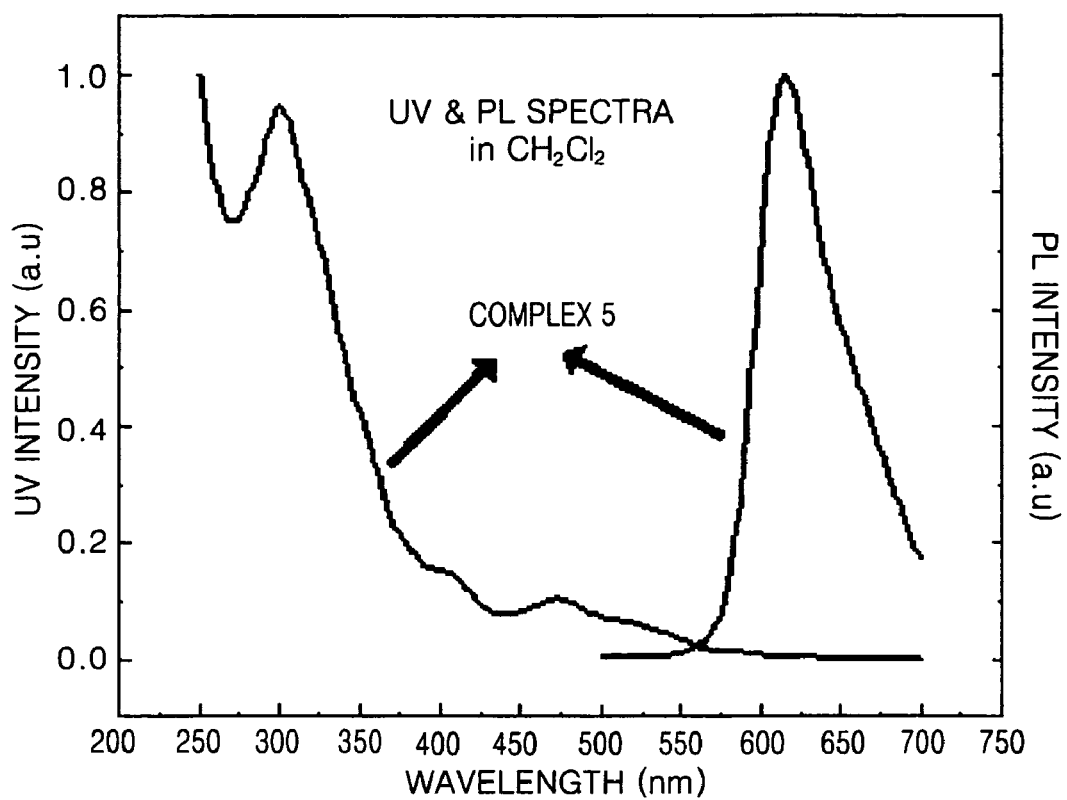
FIG. 5 is a graph showing results of UV and PL tests of Complex 5 according to an embodiment of the present invention.
Figure 6:
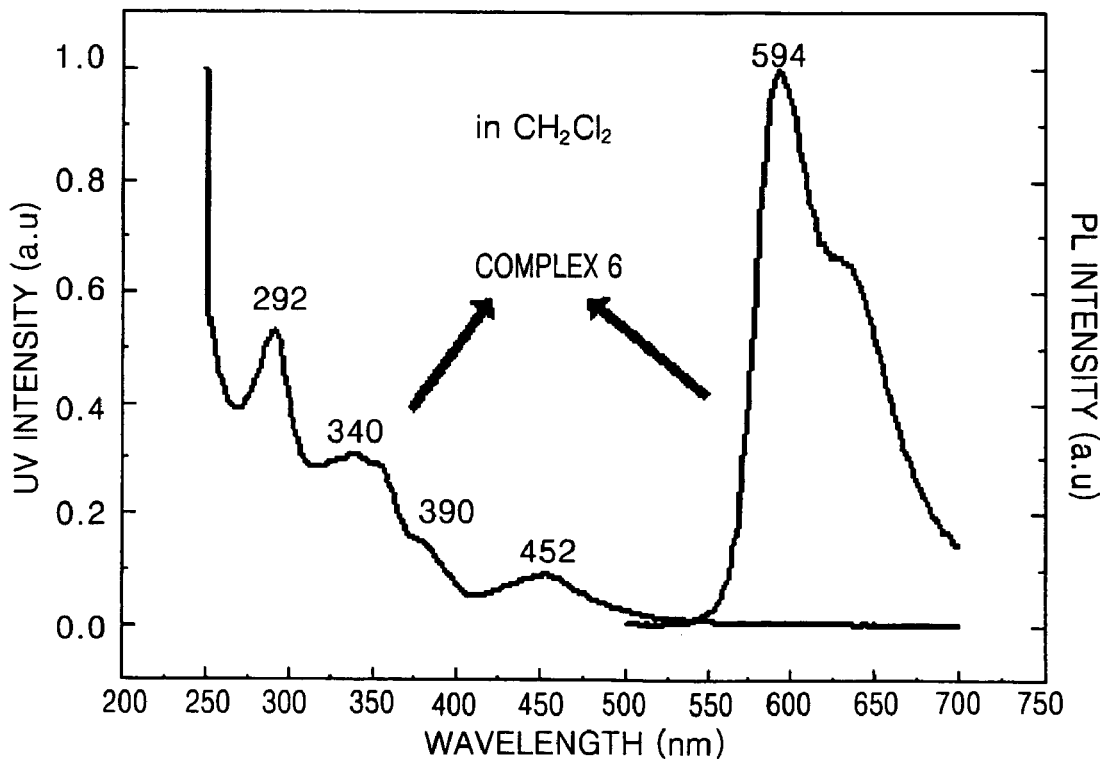
FIG. 6 is a graph showing results of UV and PL tests of Complex 6 according to an embodiment of the present invention.

635 mg (0.5 mmol) of [Ir(Piq)$_2$Cl]$_2$ prepared according to Synthesis Example 1 and 145 mg (1.1 mmol) of a lithium salt of 1-methylimidazole-2-carboxylate were dissolved in a chloroform solution in a 100 ml two-neck flask with a thermometer, a mechanical agitator, and a reflux condenser in a nitrogen atmosphere and then reacted at 50° C. for 18 hours. When the reaction was completed, the reaction product was cooled to room temperature and then the solvent used was removed under a vacuum. A residual solid formed by the reaction was dissolved in chloroform and then the melted portion of the residual solid was filtered by column chromatography to purify and isolate the desired product. At this time, the eluent used was a solution of n-hexane and ethylacetate (or chloroform and methanol) in a ratio of 10:1. The final product was Complex 2 obtained in the form of a pure red solid, and the yield thereof was 62%. Complex 2 was identified using $^1$H NMR. FIG. 2 shows results of a $^1$H NMR of Complex 2.

$^1$H-NMR(CDCl$_3$, ppm): 8.93[m, 2H], 8.73[d, 1H], 8.17 [dd, 2H], 7.91[m, 1H], 7.89[m, 1H], 7.67[m, 5H], 7.47[d, 1H], 7.26[d, 1H], 6.93[m, 2H], 6.78[d, 1H], 6.67[m, 2H], 6.51[dd, 1H], 6.28[d, 1H], 6.24[dd, 1H], 4.08[s, 3H]

Example 2

Synthesis of Complex 3 represented by Formula 3

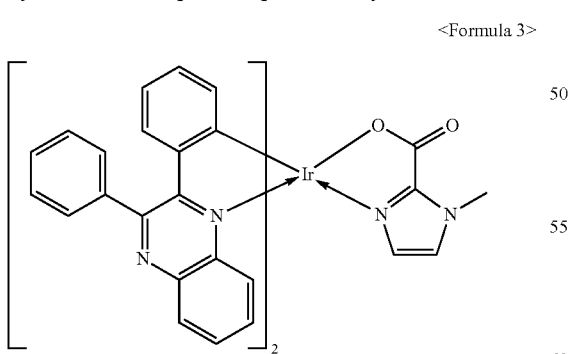

<Formula 3>

493 mg of Complex 3 (yield: 56%) was obtained in form of a pure deep red solid in the same manner as in Example 1, except that 790 mg (0.5 mmol) of [(DPQX)$_2$IrCl]$_2$ prepared according to Synthesis Example 2 was used instead of [(Piq)$_2$IrCl]$_2$ prepared according to Synthesis Example 1. Complex 3 was identified using $^1$H NMR.

$^1$H-NMR(CDCl$_3$, ppm): 8.63[m, 1H], 8.08[dd, 1H], 8.02 [m, 1H], 7.98[dd, 2H], 7.82 [br, 2H], 7.72~7.53[m, 10H], 7.14[td, 1H], 7.02[m, 2H], 6.95[d, 1H], 6.82[d, 1H], 6.62~6.41[m, 5H], 6.20[dd, 1H], 3.78 [s, 3H]

Example 3

Synthesis of Complex 4 represented by Formula 4

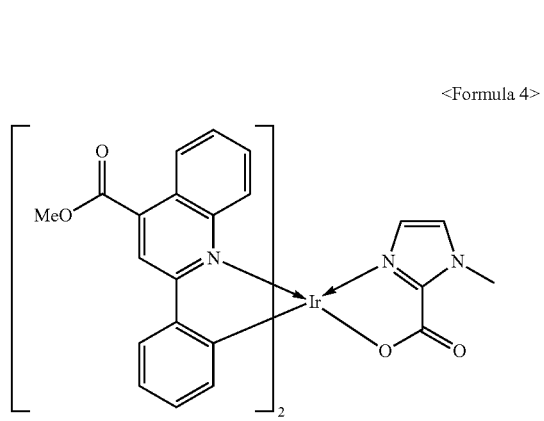

<Formula 4>

506 mg of Complex 4 (yield: 60%) was obtained in a form of a pure reddish brown solid in the same manner as in Example 1, except that 752 mg (0.5 mmol) of ([Ir(MPQC)$_2$Cl]$_2$) prepared according to Synthesis Example 3 was used instead of [(Piq)$_2$IrCl]$_2$ prepared according to Synthesis Example 1. Complex 4 was identified using $^1$H NMR.

$^1$H-NMR(CD$_2$Cl$_2$, ppm): 8.72[d, 2H], 8.56[s, 2H], 7.99[d, 2H], 7.61[s, 2H], 7.54 [m, 2H], 7.28[td, 2H], 7.14[td, 2H], 6.81[td, 2H], 6.49[d, 2H], 6.42[d, 2H], 4.12[s, 6H], 4.05[s, 3H].

Example 4

Synthesis of Complex 5 represented by Formula 5

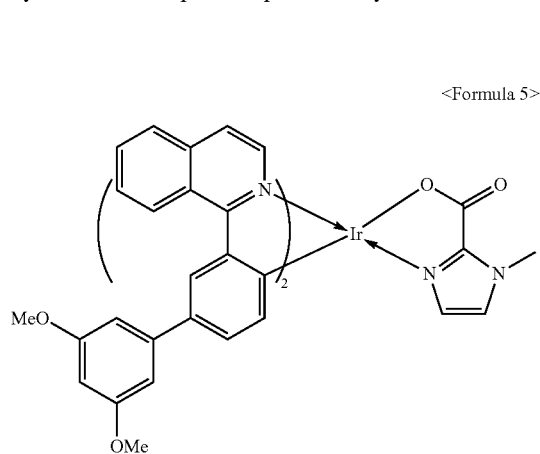

<Formula 5>

453 mg of Complex 5 (yield: 49%) was obtained in a form of a pure red solid in the same manner as in Example 1, except that 836 mg (0.5 mmol) of ([Ir(DMPPiq)$_2$Cl]$_2$) prepared according to Synthesis Example 4 was used instead of [(Piq)$_2$IrCl]$_2$ prepared according to Synthesis Example 1. Complex 5 was identified using $^1$H NMR.

$^1$H-NMR(CD$_2$Cl$_2$, ppm): 9.05[m, 2H], 8.72[d, 1H], 8.45 [dd, 2H], 7.99[td, 2H], 7.76 [m, 6H], 7.60[d, 1H], 7.46[d, 1H], 6.97[dt, 2H], 6.88[d, 1H], 6.70[dd, 4H], 6.58[d, 1H], 6.40[m, 3H], 4.09[s, 3H], 3.80[d, 12H]

Example 5

Synthesis of Complex 6 represented by Formula 6

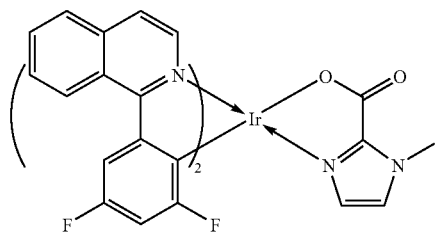

<Formula 6>

462 mg of Complex 6 (yield: 58%) was obtained in a form of a pure orange solid in the same manner as in Example 1, except that 707 mg (0.5 mmol) of ([Ir(F2Piq)$_2$Cl]$_2$) prepared according to Synthesis Example 5 was used instead of [(Piq)$_2$IrCl]$_2$ prepared according to Synthesis Example 1. The Complex 6 was identified using $^1$H NMR.

$^1$H-NMR(CD$_2$Cl$_2$, ppm): 8.90[m, 2H], 8.67[d, 1H], 8.02-7.91[m, 4H], 7.77[m, 4H], 7.63 [d, 1H], 7.52[d, 1H], 7.37[d, 1H], 6.85[d, 1H], 6.41[d, 1H], 6.39~6.26 [m, 2H], 4.01 [s, 3H]

Example 6

Synthesis of Complex 7 represented by Formula 7

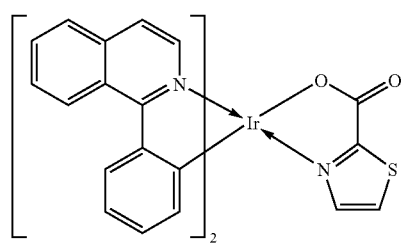

<Formula 7>

635 mg (0.5 mmol) of [Ir(Piq)$_2$Cl]$_2$ prepared according to Synthesis Example 1, 155 mg (1.2 mmol) of 2-thiazolcarboxylic acid, and 245 mg (2.5 mmol) of K$_2$CO$_3$ were dissolved in a mixture solution of chloroform and methanol in a ratio of 2:1 in a 100 ml two-neck flask with a thermometer, a mechanical agitator, and a reflux condenser in a nitrogen atmosphere and then reacted at 50° C. for 18 hours. When the reaction was completed, the reaction product was cooled to room temperature and then all of the solvent used was removed in a vacuum. The residual solid was dissolved in chloroform and then the melted portion of the residual solid was filtered by column chromatography to purify and isolate the desired product. At this time, the eluent used was a mixture solution of n-hexane and ethylacetate in a ratio of 10:1.

The final product was Complex 7 obtained in the form of a pure red solid and the yield thereof was 55%. Complex 7 was identified using $^1$H NMR.

Example 7

Synthesis of Complex 8 represented by Formula 8

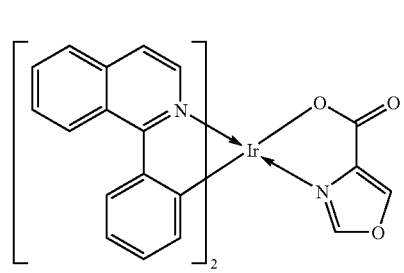

<Formula 8>

Complex 8 (yield: 58%) was obtained in a form of a pure red solid in the same manner as in Example 6, except that 4-oxacarboxylic acid was used instead of 2-thiazolcarboxylic acid. Complex 8 was identified using $^1$H NMR.

Example 8

Synthesis of Complex 9 represented by Formula 9

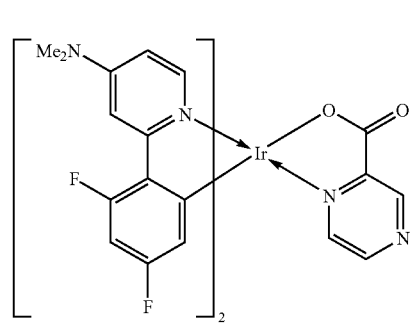

<Formula 9>

666 mg (0.5 mmol) of [Ir(DMAF$_2$Ppy)$_2$Cl]$_2$ prepared according to Synthesis Example 6, 148 mg (1.2 mmol) of 2-pyrazincarboxylic acid, and 245 mg (2.5 mmol) of K$_2$CO$_3$, were dissolved in a solution of chloroform and methanol in a ratio of 2:1 in a 100 ml two-neck flask with a thermometer, a mechanical agitator, and a reflux condenser in a nitrogen atmosphere and then reacted at 50° C. for 18 hours. When the reaction was completed, the reaction product was cooled to room temperature and then all of the solvent used was removed in a vacuum. The residual solid was dissolved in chloroform and then the melted portion of the residual solid was filtered by column chromatography to purify and isolate the desired product. At this time, the eluent used was a solution of n-hexane and ethylacetate in a ratio of 10:1. The final product was Complex 9 obtained in the form of a pure yellow solid and the yield thereof was 56%. Complex 9 was identified using ¹H NMR.

Comparative Example 1

Synthesis of Complex 10 [Ir(Piq)₃] represented by Formula 10

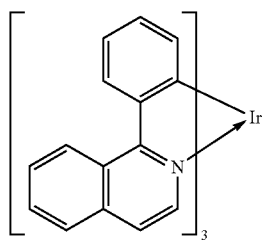

<Formula 10>

245 mg (0.5 mmol) of Ir(acac)₃ and 615 mg (3.0 mmol) of 2-phenylisoquinoline were dissolved in a glycerol solution in a 100 ml two-neck flask with a thermometer, a mechanical agitator, and a reflux condenser in a nitrogen atmosphere and then reacted at 200° C. for 26 hours. When the reaction was completed, water was added thereto to form precipitates and then filtered. The obtained solid was washed with cold methanol and diethylether, and then melted with chloroform. The melted part of the solid was purified using column chromatography. The eluent was a solution of chloroform and methanol in a ratio of 10:1. The final product was Complex 10 obtained in the form of a pure red solid and the yield thereof was 43%.

Comparative Example 2

Synthesis of Complex 11 [Ir(Piq)₂(acac)] Represented by Formula 11

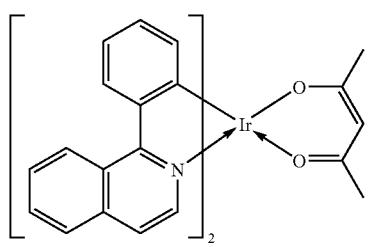

<Formula 11>

635 mg (0.5 mmol) of [Ir(Piq)₂Cl]₂ according to Synthesis Example 1, 120 mg (1.2 mmol) of 2,4-pentadion, and 245 mg (2.5 mmol) of K₂CO₃ were dissolved in a mixture solution of chloroform and methanol in a ratio of 2:1, and then reacted at 50° C. for 18. When the reaction was completed, all of the solvent used was removed under vacuum. The residual solid was dissolved in chloroform and then the melted portion of the residual solid was purified by column chromatography. At this time, the eluent used was a solution of n-hexane and ethylacetate in a ratio of 10:1. The final product was Complex 11 obtained in the form of a pure red solid and the yield thereof was 73%.

Measurement Example 1

Luminous Properties of Complexes

Luminous properties of Complex 2 were measured using an absorption spectrum and a photoluminescence (PL) spectrum. First, Complex 2 was diluted with trichloromethane to obtain a concentration of 0.2 mM, and then the absorption spectrum of the diluted Complex 2 was measured using a shimadzu UV-350 spectrometer. Meanwhile, Complex 2 was diluted with trichloromethane to obtain a concentration of 10 mM, and then the PL spectrum of the diluted Complex 2 was measured using an ISC PC1 spectrofluorometer with a Xenon lamp. Results are shown in Table 1 and FIG. 3. The absorption spectra and PL spectra of Complexes 3 through 9 were measured in the same manner as described above, except that Complex 5 was diluted with dichloromethane. Results for Complexes 3 through 6 are shown in FIGS. 3 through 6.

TABLE 1

| Complex No | Maximum Absorption Wavelength for MLCT (nm) | Maximum PL Wavelength (nm) |
| --- | --- | --- |
| 2 | 344 | 606 |
| 3 | 394 | 641 |
| 4 | 366 | 669 |
| 5 | 400 | 616 |
| 6 | 340 | 594 |
| 7 | 359 | 632 |
| 8 | 355 | 624 |
| 9 | 336 | 576 |

Measurement 2

Luminous Quantum Efficiencies (PLQE) of Complexes

A sample of each of Complexes 2, 10, and 11 was coated on a quartz substrate, installed inside an integrating sphere and was exposed to an excitation light of a UV cw laser (wavelength 325 nm). Then, the exciting PL wavelength and absorbed excitation light were measured using a spectroscope. The absolute measurement of the quantum efficiency was obtained based on [the number of photons of excited PL light/the number of photons of absorbed excitation light] that was obtained above.

TABLE 2

| | Photoluminescence Quantum Efficiency (%) | |
| --- | --- | --- |
| Complex No | Average value | Average deviation |
| 2 | 35.0 | 1.9 |
| 10 | 34.1 | 1.4 |
| 11 | 27.9 | 2.1 |

As shown in Table 2, Complex 2 according to the embodiment of the present invention showed better photoluminescence quantum efficiency than Complexes 10 and 11 prepared according to Comparative Examples.

Measurement Example 2

Characteristics of Devices Manufactured Using the Complexes

An organic light emitting device having the flowing structure was manufactured using Complex 2 as a dopant of an emission layer thereof:

ITO/PEDOT(50 nm)/CBP+PVK+Complex2(60 nm)/
BAlq3(30 nm)/LiF(0.8 nm)/Al(200 nm).

A 15 Ω/cm² (1200 Å) ITO glass substrate that was produced by Corning Inc. was cut to a size of 50 mm×50 mm×0.7 mm, and then ultrasonically cleaned with isopropyl alcohol for 5 minutes, ultrasonically cleaned with pure water for five minutes, and then cleaned with UV ozone for 30 minutes. PEDOT-PSS (AI4083) produced by Bayer Inc. was coated on the substrate and then heat treated at 120° C. for 5 hours to form a hole injection layer having a thickness of 50 nm. 71.5 wt % of CBP, 22.5 wt % of PVK, and 6 wt % of Complex 2 were mixed and then spin coated on the hole injection layer and heat treated at 110° C. for 2 hours to form an emission layer having a thickness of 60 nm. Then, a BCP compound was vacuum deposited on the emission layer to a thickness of 30 nm to form a hole blocking layer. LiF and Al were sequentially vacuum deposited on the hole blocking layer to form an electron injection layer having a thickness of 1 nm and a cathode having a thickness of 200 nm, respectively. As a result, an organic light emitting device having a structure as illustrated in FIG. 1C was manufactured. The organic light emitting device prepared will now be referred to as Sample 2.

Organic light emitting devices were manufactured using Complexes 3 through 11 in the same manner as described above. These organic light emitting devices will be referred to as Samples 3 through 11, respectively.

Operating voltages, brightnesses, and efficiencies of Samples 2 through 11 were measured using a PR650 (Spectroscan) Source Measurement Unit.

TABLE 3

| Sample No. | Operating Voltages(V) | Maximum Current Efficiency (Cd/A) | Maximum external quantum efficiency(%) | Color Coordinate (10 mA/cm²) |
|---|---|---|---|---|
| 2 | 8 | 5.1 | 6.7 | (0.63, 0.33) |
| 3 | 10 | 3.1 | 4.6 | (0.68, 0.33) |
| 4 | 10 | 2.1 | 3.5 | (0.68, 0.32) |
| 5 | 9 | 4.8 | 6.3 | (0.65, 0.34) |
| 6 | 8 | 5.8 | 7.5 | (0.63, 0.36) |
| 7 | 11 | 3.7 | 5.1 | (0.64, 0.33) |
| 8 | 10 | 3.5 | 5.0 | (0.65, 0.32) |
| 9 | 10 | 3.3 | 4.1 | (0.45, 0.48) |
| 10 | 8 | 4.5 | 6.4 | (0.67, 0.33) |
| 11 | 6 | 3.0 | 4.5 | (0.65, 0.35) |

A cyclometalated transition metal complex according to the embodiments of the present invention includes a new ancillary ligand having a carboxylic acid or the like connected to a hetero ring, so that it can efficiently emit red phosphor light through intersystem crossing (ISC) to triplets and then metal to ligand charge transfer (MLCT). An organic light emitting device manufactured using the transition metal complex shows excellent luminous efficiency and external quantum efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cyclometalated transition metal complex represented by Formula 1:

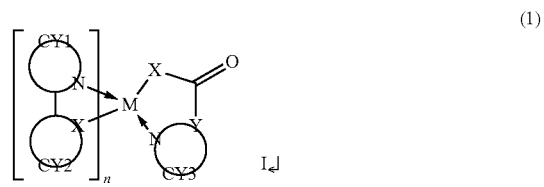

where M is a transition metal;

is a first mono anionic bidentate chelating ligand;

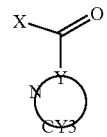

is a second mono anionic bidentate chelating ligand selected from the group consisting of ligands represented by formulae below:

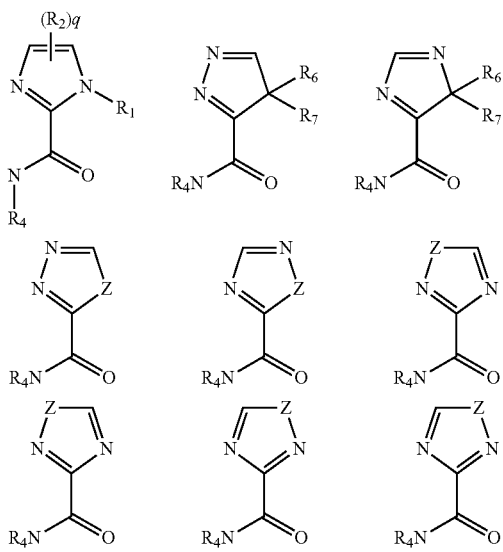

-continued

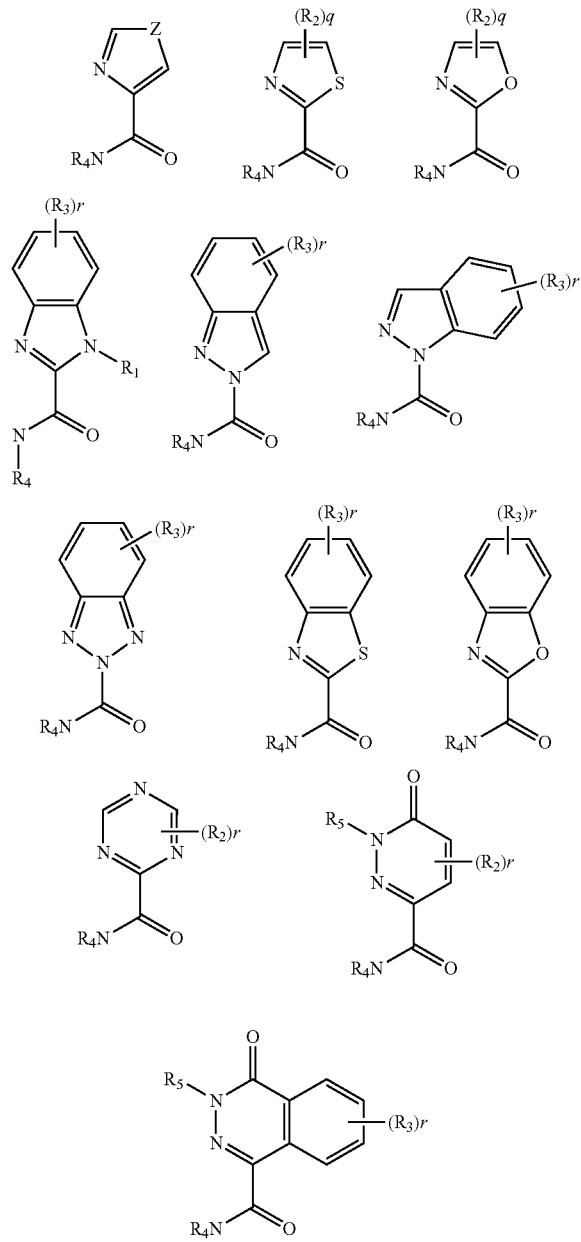

q is an integer of 0 to 5;

Z is O, S, or NR$_4$;

r is an integer of 0 to 5; and

R$_1$ through R$_8$ are each independently halogen, CF$_3$, CN, silyl, alkyl, aryl, arylalkyl, alkoxy, aryloxy, amino, or arylene, wherein the aryl, the arylalkyl, and the aryloxy can be each independently substituted with halogen, CF$_3$, CN, silyl, alkyl, aryl, alkoxy, aryloxy, amino, or arylene, and adjacent Rs may be fused together to form a five to seven-membered aliphatic or aromatic ring;

X and Y are each independently C, S, O, or N;

CY1, CY2, and CY3 are each independently aromatic or aliphatic rings; and n is 1 or 2.

2. The cyclometalated transition metal complex of claim 1, wherein the first mono anionic bidentate chelating ligand is selected from the group consisting of ligands represented by formulae below:

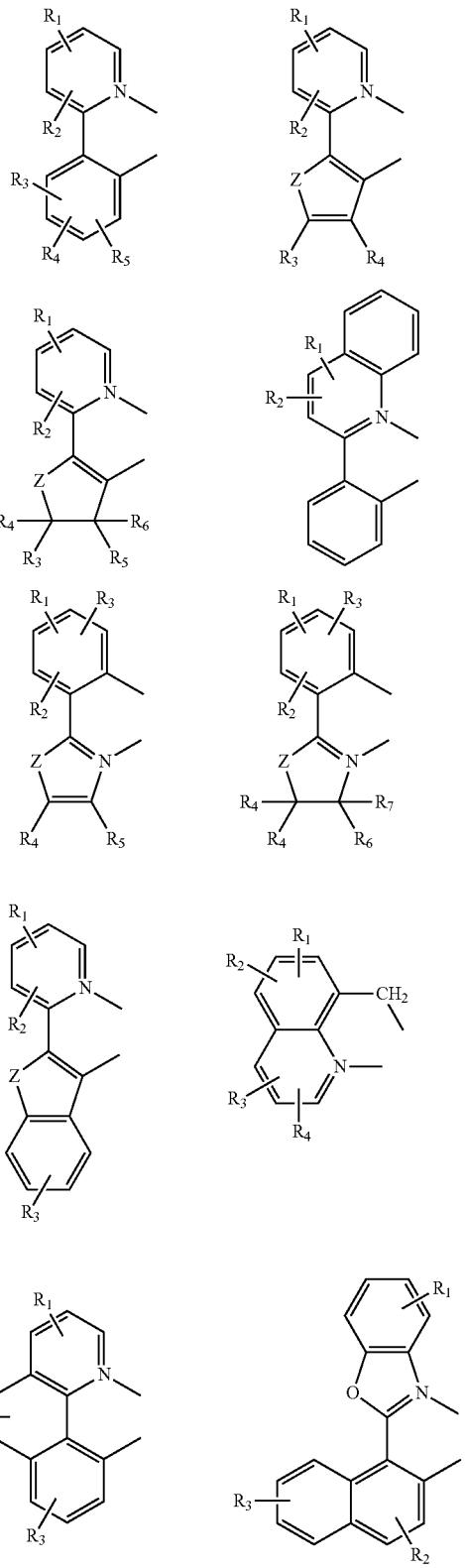

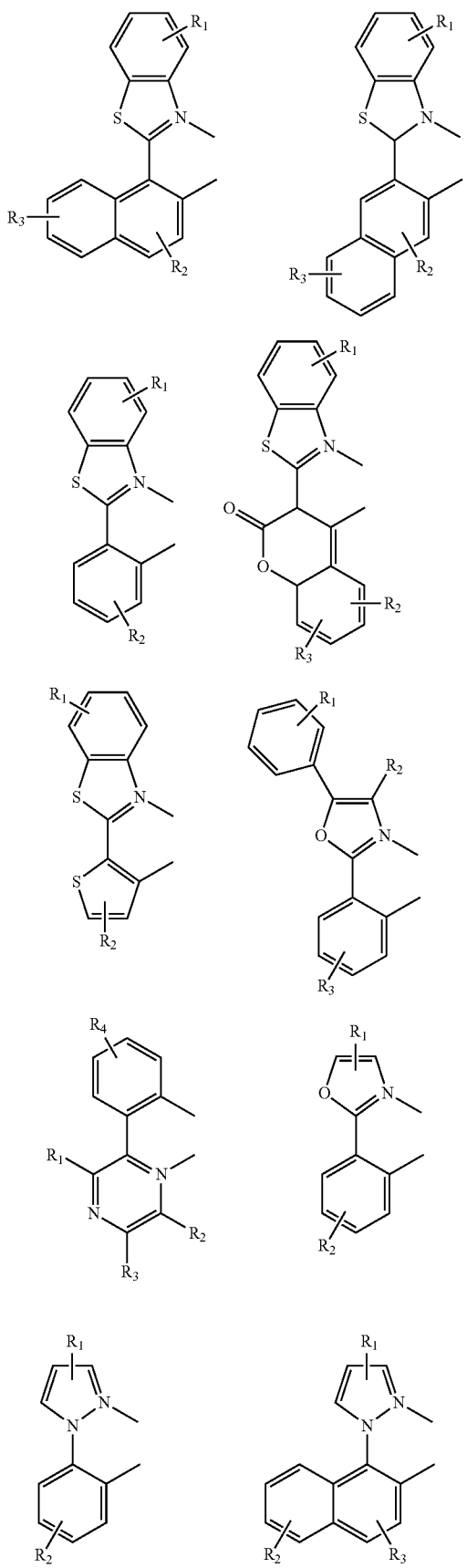

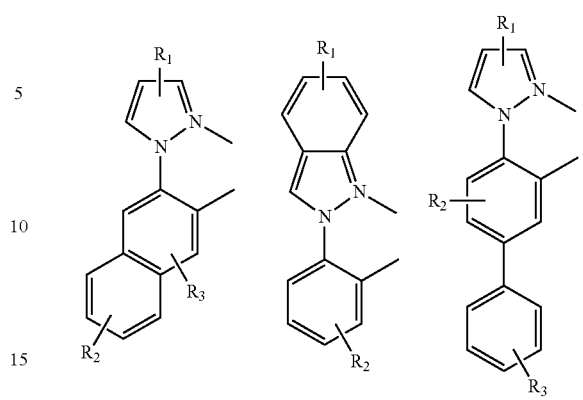

where Z is S, O, or $NR_8$; and $R_1$, $R_2$, $R_3$, $R_4$, $R_5$, $R_6$, $R_7$, and $R_8$ are each independently hydrogen, halogen, carboxylic acid alkyl ester, $CF_3$, CN, silyl, alkyl, aryl, alkoxy, aryloxy, amino, or arylene, where the aryl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five to seven membered aliphatic or aromatic ring.

3. The cyclometalated transition metal complex of claim 1, wherein the second mono anionic bidentate chelating ligand is selected from the group consisting of ligands represented by formulae below:

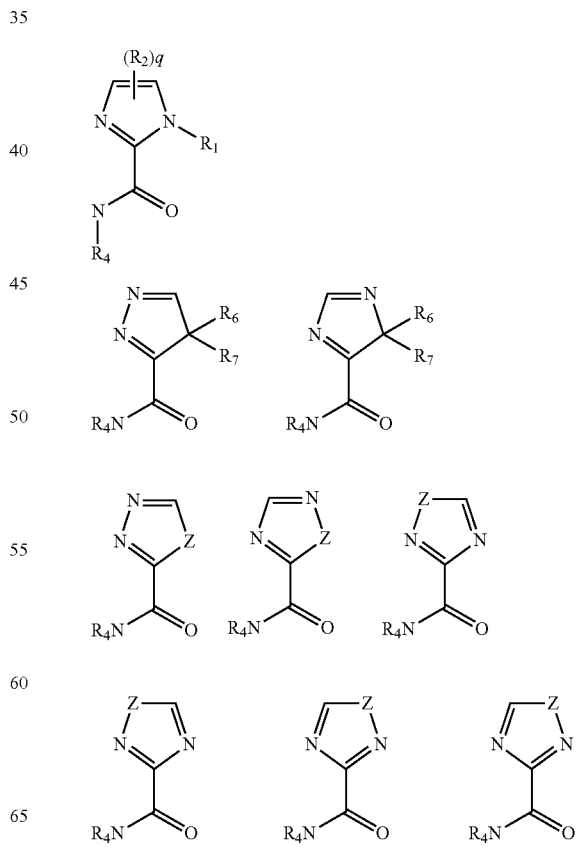

-continued

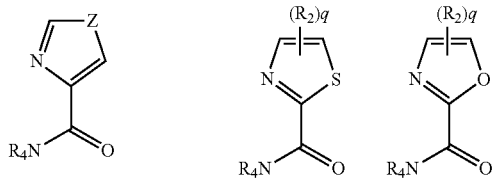

where q is an integer of 0 to 5;

Z is O, S, or NR$_4$; and

R$_1$ through R$_8$ are each independently halogen, CF$_3$, CN, silyl, alkyl, aryl, arylalkyl, alkoxy, aryloxy, amino, or arylene, wherein the aryl, the arylalkyl, and the aryloxy can be each independently substituted with halogen, CF$_3$, CN, silyl, alkyl, aryl, alkoxy, aryloxy, amino, or arylene, and adjacent Rs may be fused together to form a five to seven membered aliphatic or aromatic ring.

4. The cyclometalated transition metal complex of claim 1, wherein the second mono anionic bidentate chelating ligand is selected from the group consisting of ligands represented by formulae below:

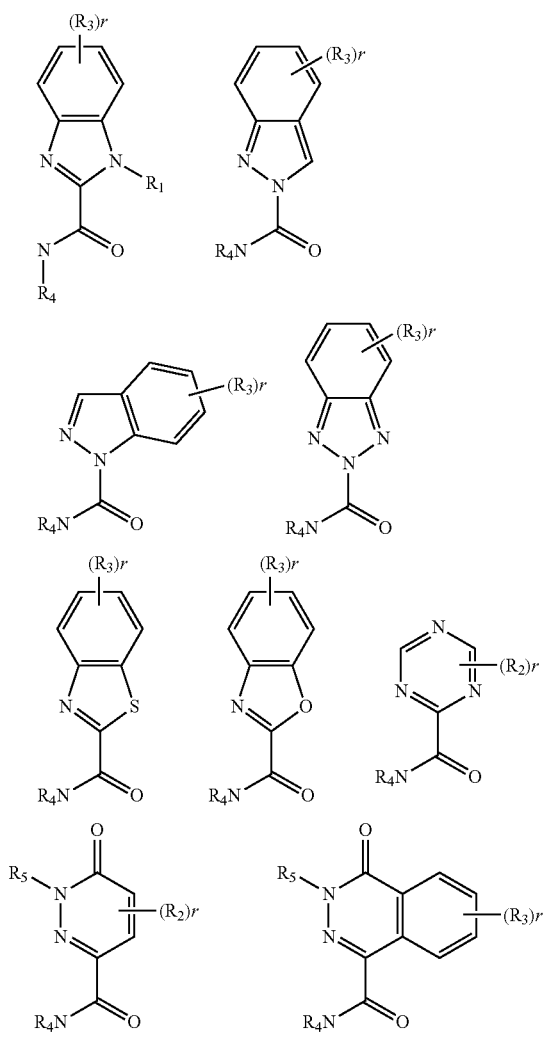

where r is an integer of 0 to 5; and

R$_1$ through R$_8$ are each independently halogen, CF$_3$, CN, silyl, alkyl, aryl, arylalkyl, alkoxy, aryloxy, amino, or arylene, wherein the aryl, the arylalkyl, and the aryloxy can be each independently substituted with halogen, CF$_3$, CN, silyl, alkyl, aryl, alkoxy, aryloxy, amino, or arylene, and adjacent Rs may be fused together to form a five to seven membered aliphatic or aromatic ring.

5. The cyclometalated transition metal complex of claim 1, wherein M is Ru, Rh, Os, Ir, Pt, or Au.

6. The cyclometalated transition metal complex of claim 1, wherein M is Ir.

7. An organic light emitting device comprising an organic layer interposed between a pair of electrodes, the organic layer comprising the cyclometalated transition metal complex of claim 1.

8. The organic light emitting device of claim 7, wherein the organic layer further comprises at least one material selected from the group consisting of at least one kind of polymer host, a mixture of a polymer host and a low molecular weight host, a low molecular weight host, and a non-luminous polymer matrix.

9. The organic light emitting device of claim 7, wherein the organic layer further comprises a green light emitting material or a blue light emitting material.

10. A cyclometalated transition metal complex represented by one of Formulae 2 through 8:

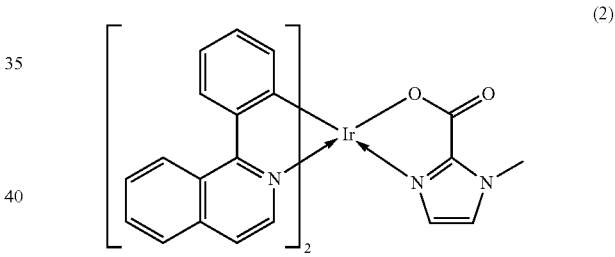

(2)

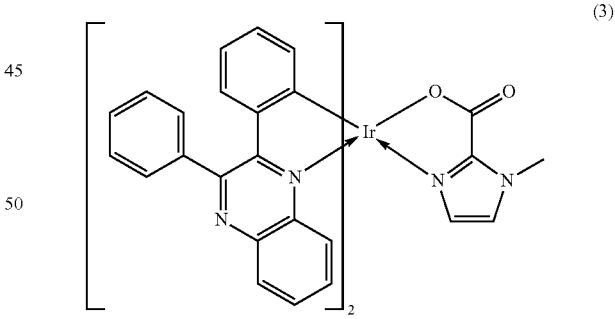

(3)

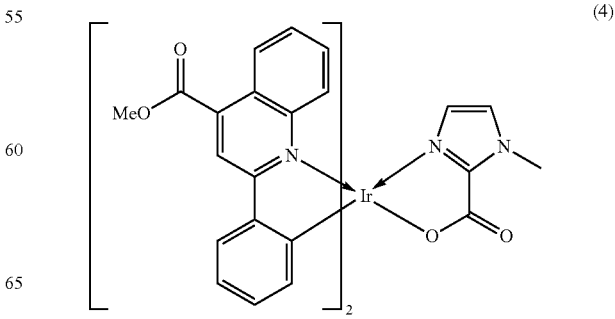

(4)

(5)

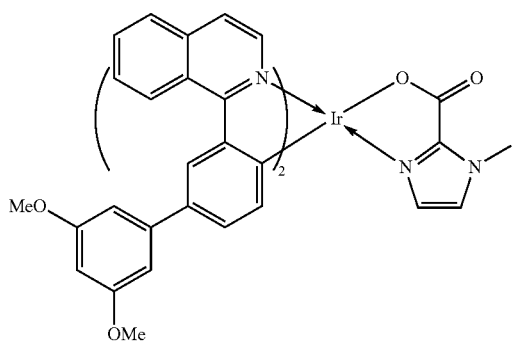

(6)

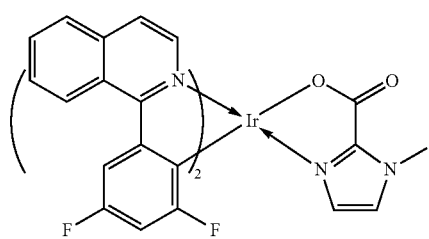

(7)

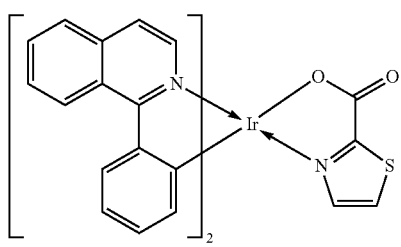

(8)

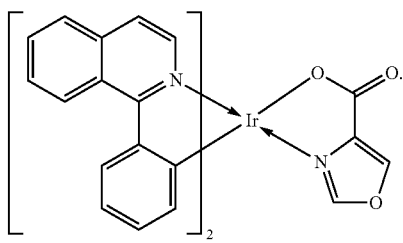

11. An organic light emitting device comprising a pair of electrodes and an organic layer interposed between the pair of electrodes, the organic layer comprising an emission layer comprising a red light emitting material comprised of the cyclometalated transition metal complex of claim 10.

12. An organic light emitting device, comprising:
a pair of electrodes; and
an organic layer interposed between the pair of electrodes, the organic layer comprising an emission layer comprising a red light emitting material comprised of a cyclometalated transition metal complex represented by Formula 1:

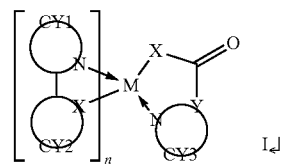 (1)

where M is a transition metal;

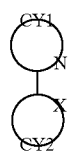

is a first mono anionic bidentate chelating ligand;

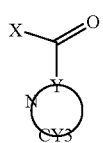

is a second mono anionic bidentate chelating ligand selected from the group consisting of ligands represented by formulae below:

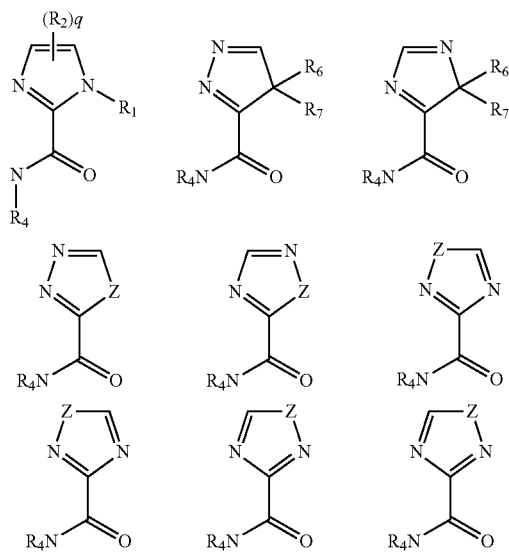

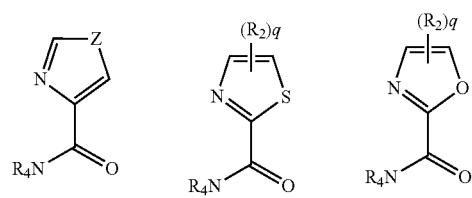

-continued

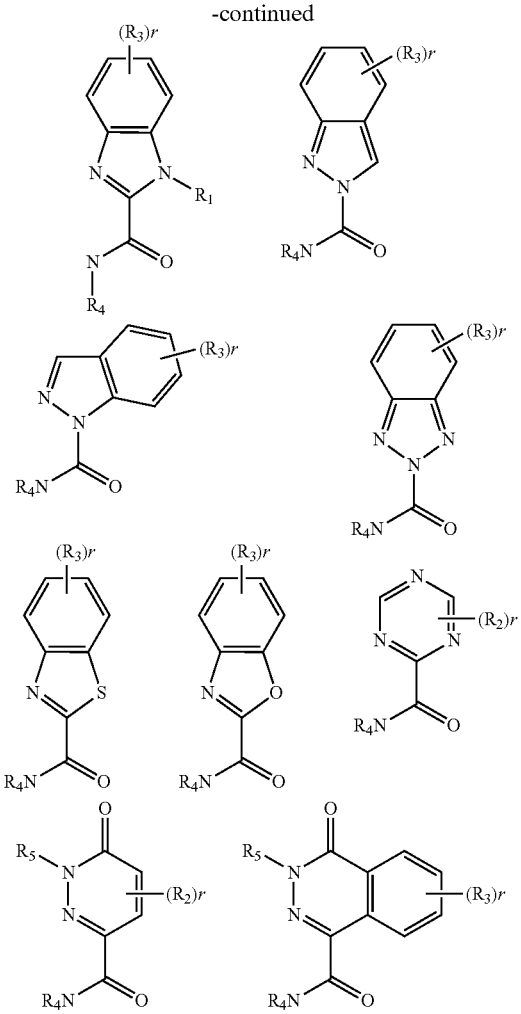

q is an integer of 0 to 5;
Z is O, S, or NR$_4$;
r is an integer of 0 to 5; and
R$_1$ through R$_8$ are each independently halogen, CF$_3$, CN, silyl, alkyl, aryl, arylalkyl, alkoxy, aryloxy, amino, or arylene, wherein the aryl, the arylalkyl, and the aryloxy can be each independently substituted with halogen, CF$_3$, CN, silyl, alkyl, aryl, alkoxy, aryloxy, amino, or arylene, and adjacent Rs may be fused together to form a five to seven membered aliphatic or aromatic ring;
X and Y are each independently C, S, O, or N;
CY1, CY2, and CY3 are each independently aromatic or aliphatic rings; and
n is 1 or 2.

13. The organic light emitting device of claim 12, wherein the content of the cyclometalated transition metal complex is in the range of 1 to 30 parts by weight based on 100 parts by weight of the total weight of material of the emission layer.

14. The organic light emitting device of claim 12, wherein the emission layer further comprises at least one material selected from the group consisting of at least one kind of polymer host, a mixture of a polymer host and a low molecular weight host, a low molecular weight host, and a non-luminous polymer matrix.

15. The organic light emitting device of claim 12, wherein the emission layer further comprises at least one of a green light emitting material or a blue light emitting material.

16. An organic light emitting device, comprising:
a first electrode;
a second electrode; and
an organic layer interposed between the first electrode and the second electrode, the organic layer comprising an emission layer comprising a red light emitting material comprised of a cyclometalated transition metal complex represented by Formula 1:

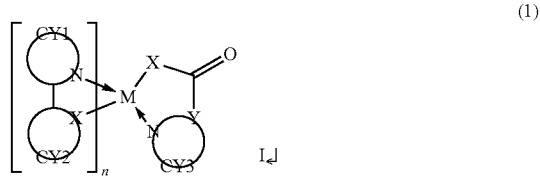

(1)

where M is a transition metal;

is selected from the group consisting of ligands represented by formulae below:

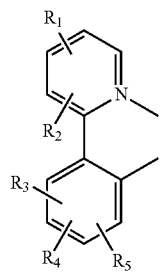 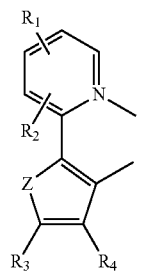

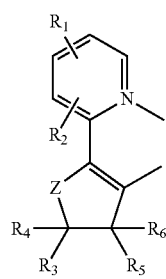 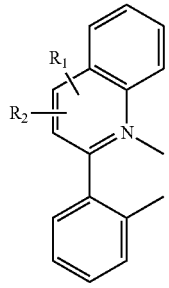

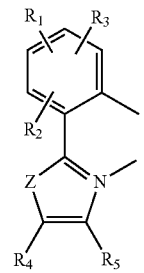 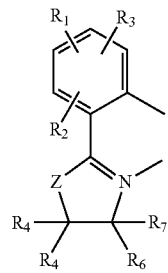

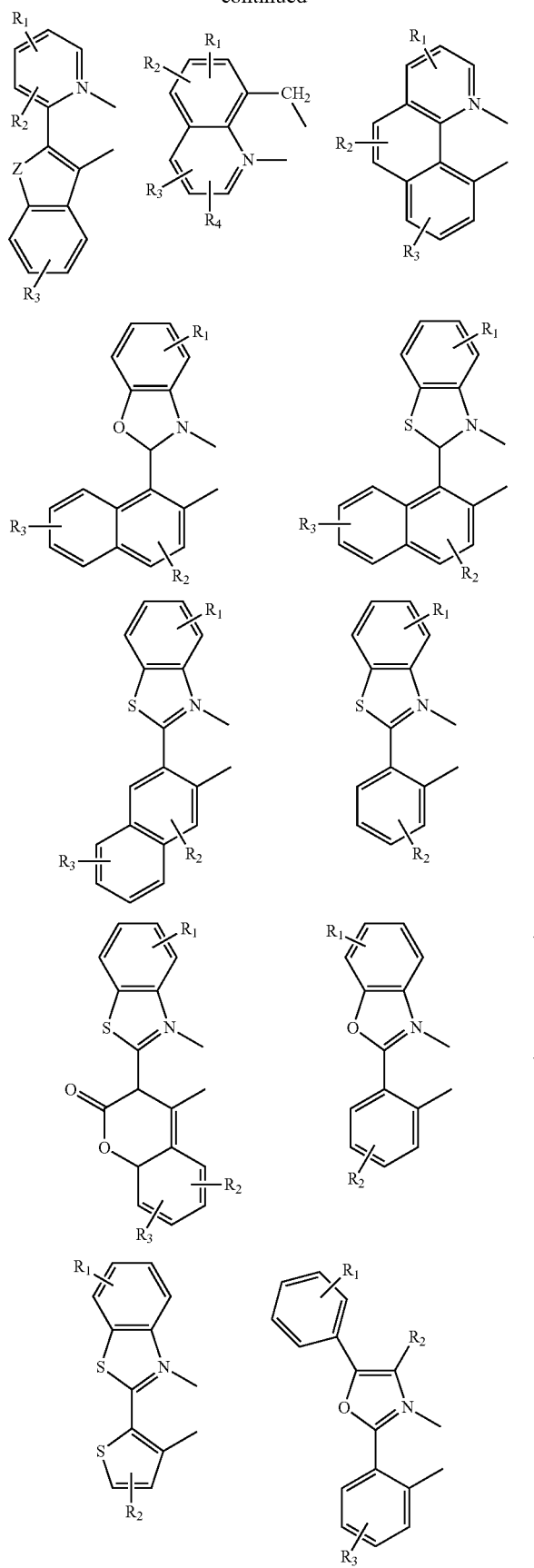
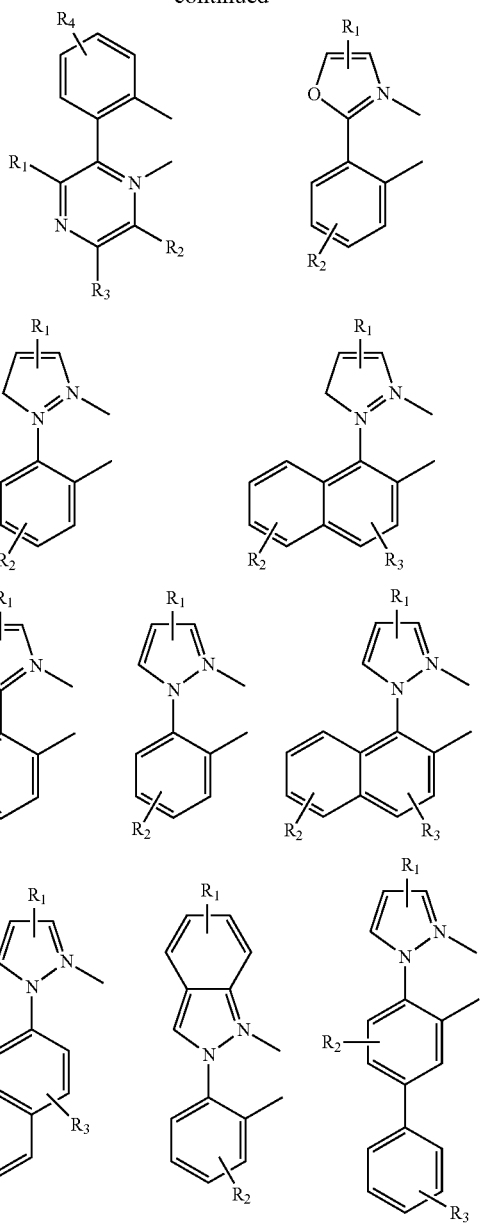

where Z is S, O, or NR$_8$; and

R$_1$, R$_2$, R$_3$, R$_4$, R$_5$, R$_6$, R$_7$, and R$_8$ are each independently hydrogen, halogen, carboxylic acid alkyl ester, CF$_3$, CN, silyl, alkyl, aryl, alkoxy, aryloxy, amino, or arylene, where the aryl, the arylalkyl, and the aryloxy can be each independently substituted with halogen, CF$_3$, CN, silyl, alkyl, aryl, alkoxy, aryloxy, amino, or arylene, and adjacent Rs may be fused together to form a five to seven membered aliphatic or aromatic ring;

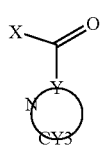

is selected from the group consisting of ligands represented by formulae below:

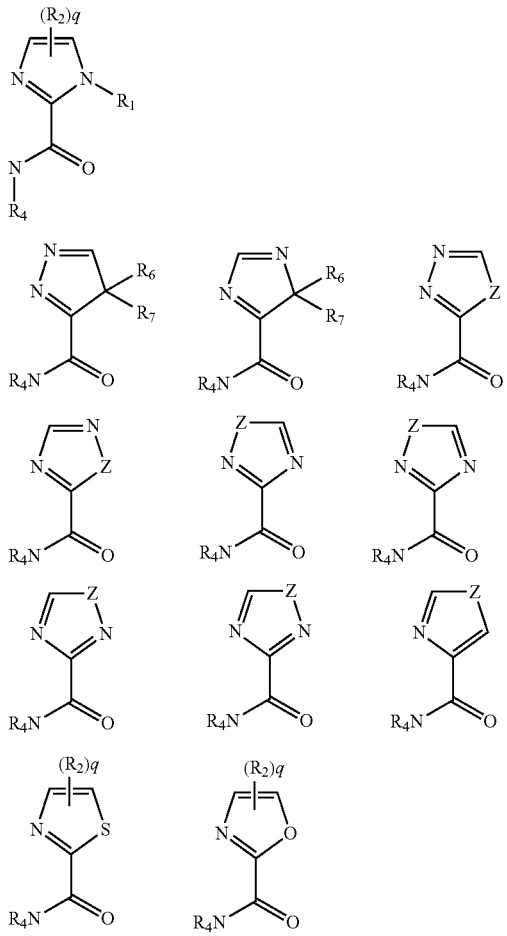

where q is an integer of 0 to 5;

Z is O, S, or $NR_4$; and $R_1$ through $R_8$ are each independently halogen, $CF_3$, CN, silyl, alkyl, aryl, arylalkyl, alkoxy, aryloxy, amino, or arylene, wherein the aryl, the arylalkyl, and the aryloxy can be each independently substituted with halogen, $CF_3$, CN, silyl, alkyl, aryl, alkoxy, aryloxy, amino, or arylene, and adjacent Rs may be fused together to form a five to seven membered aliphatic or aromatic ring;

X and Y are each independently C, S, O, or N; and n is 1 or 2.

17. The organic light emitting device of claim 16, wherein the emission layer further comprises at least one material selected from the group consisting of at least one kind of polymer host, a mixture of a polymer host and a low molecular weight host, a low molecular weight host, and a non-luminous polymer matrix.

18. The organic light emitting device of claim 16, wherein the emission layer further comprises at least one of a green light emitting material and a blue light emitting material.

19. The organic light emitting device of claim 16, wherein the organic layer further comprises an electron injection layer interposed between the second electrode and the emission layer, a hole blocking layer interposed between the electron injection layer and the emission layer, and a hole injection layer interposed between the emission layer and the first electrode.

20. The organic light emitting device of claim 16, wherein the content of the cyclometalated transition metal complex is in the range of 1 to 30 parts by weight based on 100 parts by weight of the total weight of the emission layer.

* * * * *